United States Patent
Cakir-Fuller et al.

(10) Patent No.: US 12,274,285 B2
(45) Date of Patent: Apr. 15, 2025

(54) DAIRY PRODUCT AND PROCESS

(71) Applicant: FONTERRA CO-OPERATIVE GROUP LIMITED, Auckland (NZ)

(72) Inventors: Esra Cakir-Fuller, Auckland (NZ); Christina Anna Petronella Koot, Auckland (NZ); Hongping Gao, Auckland (NZ); Stephen Paul Gregory, Auckland (NZ)

(73) Assignee: FONTERRA CO-OPERATIVE GROUP LIMITED, Auckland (NZ)

( * ) Notice: Subject to any disclaimer, the term of this patent is extended or adjusted under 35 U.S.C. 154(b) by 746 days.

(21) Appl. No.: 17/309,310

(22) PCT Filed: Nov. 20, 2019

(86) PCT No.: PCT/IB2019/059952
§ 371 (c)(1),
(2) Date: May 18, 2021

(87) PCT Pub. No.: WO2020/104954
PCT Pub. Date: May 28, 2020

(65) Prior Publication Data
US 2022/0000161 A1  Jan. 6, 2022

(30) Foreign Application Priority Data
Nov. 20, 2018 (NZ) ....................... 748564

(51) Int. Cl.
*A23L 33/19* (2016.01)
*A23B 70/30* (2025.01)
(Continued)

(52) U.S. Cl.
CPC .............. *A23L 33/19* (2016.08); *A23B 70/30* (2025.01); *A23L 2/66* (2013.01); *A23L 33/125* (2016.08);
(Continued)

(58) Field of Classification Search
CPC ... A23L 33/19; A23L 2/46; A23L 2/66; A23L 33/125; A23L 33/185; A23L 33/40;
(Continued)

(56) References Cited

U.S. PATENT DOCUMENTS 6,605,310 B2   8/2003   Fuchs et al.
2003/0099761 A1   5/2003   Jost
(Continued)

FOREIGN PATENT DOCUMENTS

CN   105792659 A   7/2016
CN   108094839 A   6/2018
(Continued)

OTHER PUBLICATIONS

Hays, Nicholas P., et al. "Effects of whey and fortified collagen hydrolysate protein supplements on nitrogen balance and body composition in older women." Journal of the American dietetic association 109.6 (2009): 1082-1087. (Year: 2009).*
(Continued)

*Primary Examiner* — Isaac Shomer
*Assistant Examiner* — Bryan James Rego
(74) *Attorney, Agent, or Firm* — KNOBBE, MARTENS, OLSON & BEAR, LLP

(57) ABSTRACT

Heat-treated, shelf-stable liquid nutritional compositions comprising whey protein and non-whey protein, and methods of producing and using these compositions. The compositions have a pH of from about 6.0 to about 8.0, a total protein content of at least about 6 g per 100 mL of the composition. The whey protein comprises or is provided by an ingredient that comprises heat-denaturable protein of which at least about 55% is present in a denatured state, and the non-whey protein comprises or consists of casein, or one or more non-dairy proteins, or casein and one or more non-dairy proteins.

24 Claims, 2 Drawing Sheets

(51) Int. Cl.
  *A23L 2/66* (2006.01)
  *A23L 33/00* (2016.01)
  *A23L 33/125* (2016.01)
  *A23L 33/185* (2016.01)
  *A61K 38/17* (2006.01)
  *A61P 3/00* (2006.01)

(52) U.S. Cl.
  CPC ............. *A23L 33/185* (2016.08); *A23L 33/40* (2016.08); *A61K 38/1709* (2013.01); *A61P 3/00* (2018.01); *A23V 2002/00* (2013.01)

(58) Field of Classification Search
  CPC ..... A23L 33/10; A23L 33/20; A61K 38/1709; A61P 3/00; A23V 2002/00; A23V 2200/316; A23V 2200/328; A23V 2200/332; A23V 2250/28; A23V 2250/51; A23V 2250/54246; A23V 2250/54252
  USPC .......................................................... 424/489
  See application file for complete search history.

(56) References Cited

U.S. PATENT DOCUMENTS

| | | |
|---|---|---|
| 2003/0104033 A1 | 6/2003 | Lai et al. |
| 2007/0128341 A1 | 6/2007 | Bakkene et al. |
| 2008/0206416 A1 | 8/2008 | Geiger |
| 2011/0046048 A1 | 2/2011 | Minor et al. |
| 2012/0094901 A1 | 4/2012 | Ludwig et al. |
| 2012/0114795 A1 | 5/2012 | Havea et al. |
| 2014/0314851 A1* | 10/2014 | Gulla .................... A23L 33/40 426/520 |
| 2014/0364361 A1 | 12/2014 | Minor et al. |
| 2016/0262424 A1* | 9/2016 | Mikkelsen ............. A23C 21/06 |
| 2017/0164645 A1 | 6/2017 | Bhaskar et al. |
| 2017/0347673 A1 | 12/2017 | Ollikainen et al. |
| 2018/0228196 A1 | 8/2018 | Le Fur et al. |
| 2019/0008199 A1 | 1/2019 | Le Fur et al. |

FOREIGN PATENT DOCUMENTS

| | | |
|---|---|---|
| EP | 2252167 B1 | 4/1989 |
| EP | 1972346 A1 | 9/2008 |
| EP | 1839492 B1 | 9/2011 |
| EP | 2424386 B1 | 5/2013 |
| EP | 2424384 B1 | 8/2013 |
| EP | 2612561 B1 | 11/2014 |
| EP | 2515920 B1 | 12/2014 |
| EP | 3085249 A1 | 10/2016 |
| EP | 2575830 B1 | 8/2017 |
| EP | 2584920 B1 | 12/2017 |
| EP | 2865382 B1 | 1/2018 |
| EP | 2622971 B1 | 4/2018 |
| EP | 2687106 B1 | 5/2018 |
| EP | 2934160 B1 | 11/2018 |
| EP | 3331377 B1 | 5/2019 |
| WO | WO 90/12506 A1 | 11/1990 |
| WO | WO 2002/098242 | 12/2002 |
| WO | WO 2006/034857 | 4/2006 |
| WO | WO 2006/137799 A1 | 12/2006 |
| WO | WO 2007/064225 A1 | 6/2007 |
| WO | WO 2007/110411 | 10/2007 |
| WO | WO 2007/110421 | 10/2007 |
| WO | WO 2009/011573 | 1/2009 |
| WO | WO 2009/072869 | 6/2009 |
| WO | WO 2009/072885 | 6/2009 |
| WO | WO 2009/072886 | 6/2009 |
| WO | WO 2009/113845 A1 | 9/2009 |
| WO | WO 2010/120199 | 10/2010 |
| WO | WO 2010/131952 | 11/2010 |
| WO | WO 2011/078654 | 6/2011 |
| WO | WO 2011/094544 A1 | 8/2011 |
| WO | WO 2011/152706 | 12/2011 |
| WO | WO 2012/006074 | 1/2012 |
| WO | WO 2012/106179 | 8/2012 |
| WO | WO 2013/065014 A1 | 5/2013 |
| WO | WO 2013/133727 | 9/2013 |
| WO | WO 2014/099795 | 6/2014 |
| WO | WO 2015/059243 A1 | 4/2015 |
| WO | WO 2016/102993 | 6/2016 |
| WO | WO 2016/174651 | 11/2016 |
| WO | WO 2017/115058 A1 | 7/2017 |
| WO | WO 2017/134256 | 8/2017 |
| WO | WO 2017/136197 | 8/2017 |
| WO | WO 2017/211856 A1 | 12/2017 |
| WO | WO 2018/114834 | 6/2018 |
| WO | WO 2018/130595 A1 | 7/2018 |
| WO | WO 2019/086407 | 5/2019 |
| WO | WO 2019/121855 | 6/2019 |
| WO | WO 2003/005837 A1 | 1/2023 |

OTHER PUBLICATIONS

Deeth et al, "Heat treatment of milk | ultra-high temperature treatment (UHT): heating systems", Encyclopedia of Dairy Sciences, 2011, vol. 2, pp. 699-707.
Luiking et al, "Protein type and caloric density of protein supplements modulate postprandial amino acid profile through changes in gastrointestinal behaviour: A randomized trial", Clinical Nutrition, Feb. 2016, vol. 35, No. 1, pp. 48-58, doi: 10.1016/j.clnu.2015.02.013.
Van den Braak et al. "A novel protein mixture containing vegetable proteins renders enteral nutrition products non-coagulating after in vitro gastric digestion." Clinical Nutrition, 2013, vol. 32, No. 5, pp. 765-771, doi:10.1016/j.clnu.2012.11.016.
International Preliminary Report on Patentability mailed Jan. 28, 2020 for PCT Application No. PCT/IB2019/059952 in 5 pages.
International Search Report and Written Opinion in International PCT Application No. PCT/IB2019/059952 dated Jan. 28, 2020 in 9 pages.
Extended European Search Report issued in application No. 19887395.2 on Jul. 15, 2022.
Decision of final rejection issued in Chinese application No. 201980084049.0 on Mar. 29, 2024.
Zhang Heping, editor-in-chief Zhang Liebing, "Modern Dairy Industry Handbook", China Light Industry Press, Aug. 2005, pp. 274-277.
Duoxia, "Fat Substitutes and New Technology for their Preparation", Shaanxi Science and Technology Press , p. 23 (2021).
Ipsen, "Microparticulated whey proteins for improving dairy product texture", International Dairy Journal, pp. 1-26 (2016).
Office Action issued in Chinese Application No. 201980084049.0 on Dec. 29, 2023.
Tanger et al., "Influence of Pea and Potato Protein Microparticles on Texture and Sensory Properties in a Fat-Reduced Model Milk Dessert", ACS Food Sci. Technol., 2:169-179 (2022).
Japanese Examination Report issued in application No. JP 2021-527962 on Oct. 4, 2023.
Third party observation filed in European patent application No. 19887395.2 on Jun. 6, 2024.

* cited by examiner

DAIRY PRODUCT AND PROCESS

REFERENCE TO RELATED APPLICATIONS

This application is the U.S. National Phase of International Application PCT/IB2019/059952, which is incorporated by reference herein. Any and all applications for which a foreign or domestic priority claim is identified in the Application Data Sheet as filed with the present application are hereby incorporated by reference under 37 C.F.R. § 1.57.

FIELD OF THE INVENTION

The present invention relates to high protein liquid nutritional compositions and methods for their preparation and use.

BACKGROUND TO THE INVENTION

A range of specialised foods (meal replacers, nutritional supplements and/or meal supplements) exist for the elderly or convalescents or other patients that cannot get the nutrition required by eating normal foods or are unable to feed themselves or require assistance during feeding. Generic terms used to categorise these foods include "medical foods", "enteral foods", "enteral nutrition", "medical liquids", "oral nutritional supplements", and the like, and are collectively used to refer to foods that are taken under the supervision of a medical professional. In some jurisdictions medical foods/enteral nutrition has a legal definition. In the USA, the term medical food, as defined in section 5(b) of the Orphan Drug Act (21 U.S.C. 360ee (b) (3)) is "a food which is formulated to be consumed or administered enterally under the supervision of a physician and which is intended for the specific dietary management of a disease or condition for which distinctive nutritional requirements, based on recognized scientific principles, are established by medical evaluation". In some jurisdictions, such foods are available to the public only by prescription, in others they can be procured directly over the counter (OTC).

Enteral formulas are ingested both orally and through tubes. Oral ingestion is useful when nutrient supplements are necessary and both the digestive tract and the patient are capable of taking them. Tube feeding is necessary for patients who need supplements but cannot take nutrition orally.

All these foods have very exacting requirements. They require a high degree of heat treatment to provide sterility and long shelf life stability, high calorific density, i.e. highly concentrated doses of nutrients, but at the same time low viscosity so that they can be readily administered to the patient and consumed easily.

Liquid nutritional foods are also used by healthy subjects as meal replacers or when a rapidly consumable food is required. Liquid nutritional foods are generally suitable for use by children, the aged or by athletes and for these consumers the organoleptic properties of the product such as, for instance viscosity, mouthfeel, smell and colour are very important.

Liquid nutritional foods are often calorifically dense in that they contain nutrients such as fat, protein and carbohydrates in levels and combinations to attain calorific values of at least 0.5 kcal/g or kcal/ml. In the group of medical or enteral foods calorific densities up to 3 kcal/g or even above are known. Such high calorific densities are difficult to achieve with low viscosity and sufficient protein. Hydrolysed protein may be used to achieve low viscosity. However, hydrolysed protein seriously decreases taste acceptability and therefore voluntary intake of the nutritional composition by the patient group.

Existing high-protein, high energy liquid nutritional compositions comprising greater than 10 grams protein per 100 mL of the composition primarily rely on casein as the main source of protein. High protein liquid nutritional compositions comprising casein are known to cause coagulation in the upper gastrointestinal tract, leading to delayed gastric emptying, discomfort, and reduced food intake In general terms, coagulation of milk proteins is the formation of a gel via destabilisation of casein micelles through acid and/or enzymes causing the micelles to aggregate and form a network, which partially immobilizes water and traps fat globules in the newly formed matrix. Ye reports that milk proteins, more specifically micellar or non-micellar caseins or caseinates, form a clot in the acidic stomach environment and thus are retained in the stomach for longer and delay the delivery of amino acids to the upper intestinal lumen (Ye et al., 2016. *Food Hydrocolloids*, 52: 478-486). Therefore, nutritional compositions comprising micellar and/or non-micellar casein and/or caseinates and/or milk proteins or a mixture thereof as the main protein source may cause delayed gastric emptying, which can result in upper gastrointestinal discomfort.

Whey protein is recognised as a suitable protein source to treat persons suffering from diseases or conditions or as a result of treatment for a disease or condition, such as from cachexia, sarcopenia, as well as being a valuable source of nutrition for healthy persons, such as sports people and active elderly. Whey proteins remain soluble and pass rapidly through the stomach, leading to faster delivery of amino acids to the circulation. However, the high heat treatment applied to liquid nutritional compositions (i.e. retorting or UHT) to ensure product safety and extended shelf life leads to unacceptable gelling and aggregation of compositions comprising high whey protein content. Such gelling risks extensive fouling and blocking of the production plant, particularly UHT heating equipment.

There is a need in the art for heat-treated, shelf-stable, high protein liquid nutritional compositions of neutral pH and low viscosity that do not readily coagulate in the upper gastrointestinal tract.

It is an object of the present invention to provide improved or alternative liquid nutritional compositions that go some way to meeting this need and/or overcoming the aforementioned difficulties, or to at least provide the public with a useful choice.

SUMMARY OF THE INVENTION

In one aspect the invention relates to a heat-treated, shelf-stable liquid nutritional composition having a pH of from about 6.0 to about 8.0, the composition comprising
a total protein content of at least about 6 g per 100 mL of the composition, the total protein content comprising
a) whey protein comprising or provided by an ingredient that comprises heat-denaturable protein of which at least about 55% is present in a denatured state, and
b) non-whey protein comprising or consisting of casein, or one or more non-dairy proteins, or casein and one or more non-dairy proteins.

In another aspect the invention relates to a heat-treated, shelf-stable liquid nutritional composition having a pH of from about 6.0 to about 8.0, the composition comprising
a total protein content of at least about 6 g per 100 mL of the composition, the total protein content comprising a) whey protein comprising or provided by an ingredient that comprises heat-denaturable protein of which at least about 55% is present in a denatured state, and
b) non-whey protein comprising or consisting of casein, or one or more non-dairy proteins, or casein and one or more non-dairy proteins,
wherein the whey protein has a degree of hydrolysis of less than about 4%, and the whey protein and the non-whey protein are present in a weight ratio of at least about 35:65, preferably from about 35:65 to about 80:20.

In another aspect the invention relates to a heat-treated, shelf-stable liquid nutritional composition having a pH of from about 6.0 to about 8.0, the composition comprising
a total protein content of at least about 6 g per 100 mL of the composition, the total protein content comprising
a) whey protein comprising or provided by an ingredient that comprises heat-denaturable protein of which at least about 55% is present in a denatured state, and
b) non-whey protein comprising or consisting of casein, or one or more non-dairy proteins, or casein and one or more non-dairy proteins
wherein the composition comprises at least about 4 g whey protein per 100 mL of the composition.

In a further aspect the invention relates to a heat-treated, shelf-stable liquid nutritional composition having a pH of from about 6.0 to about 8.0, the composition comprising
a total protein content of at least about 6 g per 100 mL of the composition, the total protein content comprising
a) whey protein comprising or provided by an ingredient that comprises heat-denaturable protein of which at least about 55% is present in a denatured state, and
b) non-whey protein comprising or consisting of casein, or one or more non-dairy proteins, or casein and one or more non-dairy proteins,
wherein the whey protein comprises at least about 40% by weight of the total protein in the composition.

In another aspect the invention relates to a heat-treated, shelf-stable liquid nutritional composition having a pH of from about 6.0 to about 8.0, the composition comprising
a total protein content of at least about 6 g per 100 mL of the composition, the total protein content comprising
a) whey protein comprising or provided by an ingredient that comprises heat-denaturable protein of which at least about 55% is present in a denatured state, and
b) casein.

In another aspect the invention relates to a heat-treated, shelf-stable liquid nutritional composition having a pH of from about 6.0 to about 8.0, the composition comprising
a total protein content of at least about 6 g per 100 mL of the composition, the total protein content comprising
a) whey protein comprising or provided by an ingredient that comprises heat-denaturable protein of which at least about 55% is present in a denatured state, and
b) casein,
wherein the whey protein and casein are present in a weight ratio of at least about 35:65, preferably from about 35:65 to about 80:20.

In one aspect the invention provides a method of preparing a liquid nutritional composition, the method comprising
a) providing a liquid composition having a pH of from about 6.0 and 8.0, the composition comprising
a total protein content of at least about 6 g per 100 mL of the composition, the total protein content comprising
i. whey protein comprising or provided by an ingredient that comprises heat-denaturable protein of which at least about 55% is present in a denatured state, and
ii. non-whey protein comprising or consisting of casein, or one or more non-dairy proteins, or casein and one or more non-dairy proteins, and
b) subjecting the liquid composition to a heat treatment having an $F_0$-value of at least 3 to prepare the heat-treated liquid nutritional composition.

In another aspect the invention relates to a method of preparing a heat-treated, shelf-stable liquid nutritional composition, the method comprising
a) providing a liquid composition having a pH of from about 6.0 to about 8.0, the composition comprising
a total protein content of at least about 6 g per 100 mL of the composition, the total protein content comprising
i. whey protein comprising or provided by an ingredient that comprises heat-denaturable protein of which at least about 55% is present in a denatured state, and the whey protein in a denatured state comprising microparticles having a volume weighted mean diameter D[4,3] of less than about 10 μm,
ii. non-whey protein comprising or consisting of casein, or one or more non-dairy proteins, or casein and one or more non-dairy proteins,
wherein the whey protein has a degree of hydrolysis of less than about 4%, and the whey protein and the non-whey protein are present in a weight ratio of at least about 35:65, preferably from about 35:65 to about 80:20, and
b) subjecting the liquid composition to a heat treatment having an $F_0$-value of at least 3 to prepare the heat-treated liquid nutritional composition.

In one aspect the invention provides a heat-treated liquid nutritional composition prepared according to a method described herein.

In one aspect the invention provides a method of maintaining or increasing muscle protein synthesis, maintaining or increasing muscle mass, preventing or reducing loss of muscle mass, maintaining or increasing growth, preventing or decreasing muscle catabolism, preventing or treating cachexia, preventing or treating sarcopenia, increasing rate of glycogen resynthesis, modulating blood sugar levels, increasing insulin response to raised blood glucose concentration, reducing satiety, reducing satiation, reducing food intake, reducing calorie intake, improving glucose metabolism, increasing rate of recovery following surgery, increasing prehabilitation efficacy prior to surgery or chemotherapy, increasing rate of recovery following injury, increasing rate of recovery following exercise, increasing sports performance, and/or providing nutrition to a subject in need thereof, the method comprising the steps of administering to the subject a liquid nutritional composition described herein.

In another aspect the invention provides use of a liquid nutritional composition described herein in the preparation of a composition, preferably a supplement or medicament for maintaining or increasing muscle protein synthesis, maintaining or increasing muscle mass, preventing or reducing loss of muscle mass, maintaining or increasing growth, preventing or decreasing muscle catabolism, preventing or treating cachexia, preventing or treating sarcopenia, increasing rate of glycogen resynthesis, modulating blood sugar levels, increasing insulin response to raised blood glucose concentration, reducing satiety, reducing satiation, reducing food intake, reducing calorie intake, improving glucose metabolism, increasing rate of recovery following surgery, increasing prehabilitation efficacy prior to surgery or chemotherapy, increasing rate of recovery following injury, increasing rate of recovery following exercise, increasing sports performance, and/or providing nutrition to a subject in need thereof.

In a further aspect the invention provides a liquid nutritional composition described herein for maintaining or increasing muscle protein synthesis, maintaining or increasing muscle mass, preventing or reducing loss of muscle mass, maintaining or increasing growth, preventing or decreasing muscle catabolism, preventing or treating cachexia, preventing or treating sarcopenia, increasing rate of glycogen resynthesis, modulating blood sugar levels, increasing insulin response to raised blood glucose concentration, reducing satiety, reducing satiation, reducing food intake, reducing calorie intake, improving glucose metabolism, increasing rate of recovery following surgery, increasing prehabilitation efficacy prior to surgery or chemotherapy, increasing rate of recovery following injury, increasing rate of recovery following exercise, increasing sports performance, and/or providing nutrition to a subject in need thereof.

Any of the embodiments or preferences described herein may relate to any of the aspects herein alone or in combination with any one or more embodiments or preferences described herein, unless stated or indicated otherwise.

In various embodiments the liquid nutritional composition has a pH of about 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or about 8.0, and various ranges can be selected from between these values, for example, from about 6.0 to about 8.0, about 6.0 to about 7.5, about 6.0 to about 7.2, about 6.0 to about 7.0, about 6.2 to about 8.0, about 6.2 to about 7.5, about 6.2 to about 7.2, about 6.2 to about 7.0, about 6.4 to about 8.0, about 6.4 to about 7.5, about 6.4 to about 7.2, about 6.4 to about 7.0, or from about 6.5 to about 8.0, about 6.5 to about 7.5, about 6.5 to about 7.2, or from about 6.5 to about 7.0.

In various embodiments the liquid nutritional composition comprises a total protein content of at least about 6, 7, 8, 9, 10, 11, 12, 13, 14, 15, 16, 17, 18, 19, 20, 21, 22, 23, 24, 25, 27 or at least about 30 g per 100 mL of the composition, and various ranges can be selected from between these values, for example, from about 6 to about 30 g, about 7 to about 30, about 8 to about 30, about 9 to about 30, about 10 to about 30, 6 to about 25 g, about 7 to about 25, about 8 to about 25, about 9 to about 25, about 10 to about 25, about 11 to 25, about 12 to 25, about 13 to about 25, about 14 to about 25, about 15 to about 25, about 6 to about 20 g, about 7 to about 20, about 8 to about 20, about 9 to about 20, about 10 to about 20, or about 10 to about 15 g total protein per 100 mL of the composition. In various embodiments the liquid nutritional composition comprises a total protein content of at least about 9 g protein per 100 mL of the composition, or at least about 10 g protein per 100 mL of the composition, or at least about 12 g protein per 100 mL of the composition.

In various embodiments the whey protein and non-whey protein, the whey protein and casein, or the whey protein and one or more non-dairy proteins are present in the composition in a weight ratio of at least about 20:80, 25:75, 30:70, 35:65, 40:60, 45:55, 50:50, 55:45, 60:40, 65:35, 70:30, 75:25, 80:20, 85:15, 90:10, 95:5 or at least about 99:1 and various ranges can be selected from between these values, for example, from about 30:70 to about 80:20, about 35:65 to about 80:20, about 40:60 to about 80:20, about 45:55 to about 80:20, about 50:50 to about 80:20, about 30:70 to about 75:25, about 35:65 to about 75:25, about 40:60 to about 75:25, about 45:55 to about 75:25, about 50:50 to about 75:25, about 30:70 to about 70:30, about 35:65 to about 70:30, about 40:60 to about 70:30, about 45:55 to about 70:30 or about 50:50 to about 70:30, about 30:70 to about 65:35, about 35:65 to about 65:35, about 40:60 to about 65:35, about 45:55 to about 65:35, about 50:50 to about 65:35, about 30:70 to about 60:40, about 35:65 to about 60:40, about 40:60 to about 60:40, about 45:55 to about 60:40, or about 50:50 to about 60:40. In one preferred embodiment, the ratio may be at least about 35:65, more preferably from about 35:65 to about 80:20.

In various embodiments the composition comprises at least about 0.01, 0.1, 1, 2, 3, 4, 5, 6, 7, 8, 9, 10, 11, 12, 13, 14, 15, 16, 17, 18, 19 or at least about 20 g non-whey protein per 100 mL of the composition, and various ranges may be selected from between any of these values, for example, from about 0.01 to about 2, 1 to about 20, 2 to about 20, 3 to about 20, 4 to about 20, 5 to about 20, 0.01 to about 15, 1 to about 15, 2 to about 15, 3 to about 15, 4 to about 15, 5 to about 15, 0.01 to about 10, 1 to about 10, 2 to about 10, 3 to about 10, 4 to about 10 or about 5 to about 10 g non-whey protein per 100 mL of the composition.

In various embodiments non-whey protein comprises at least about 1, 2, 5, 10, 15, 20, 25, 30, 35, 40, 45, 50, 55, 60, 65, 70, 75, 80, 85, 90 or at least about 95% by weight of the total protein in the composition, and various ranges may be selected from between any of these values, for example, from about 1% to about 99%, 10% to about 95%, about 10 to about 80%, about 10% to about 70%, about 10% to about 65%, about 10% to about 60%, about 15% to about 95%, about 15 to about 80%, about 15% to about 70%, about 15% to about 65%, about 15% to about 60%, about 20 to about 80%, about 20% to about 70%, about 20% to about 65%, or about 20% to about 60% by weight of the total protein in the composition.

In one embodiment the non-whey protein is at least partially hydrolysed. In another embodiment the non-whey protein is non-hydrolysed. In various embodiments the non-whey protein has a degree of hydrolysis of less than about 0, 1, 2, 3, 4, 5, 6, 7, 8, 9, 10, 12, 15, 20, 25, 30, 40, 50, 60, 70, 80, 90, 95 or at least about 99%, and various ranges may be selected from between any of these values, for example, from about 0 to about 99, 1 to about 99%, about 5 to about 99%, about 10 to about 99%, about 20 to about 99%, about 50 to about 99%, about 0 to about 95, about 1 to about 95%, about 5 to about 95%, about 10 to about 95%, about 20 to about 95%, about 50 to about 95%, about 0 to about 90, about 1 to about 90%, about 5 to about 90%, about 10 to about 90%, about 20 to about 90%, about 50 to about 90%, about 0% to about 50%, about 1% to about 50%, about 0% to about 25%, about 1% to about 25%, about 0% to about 20%, about 1% to about 20%, about 0% to about 10%, about 1% to about 10%, about 0% to about 5% or about 1% to about 5%.

In various embodiments, the whey protein comprises, consists essentially of, or consists of, or is provided by an ingredient that comprises, consists essentially of, or consists of heat-denaturable protein of which at least about 55%, 60%, 65%, 70%, 75%, 80%, 85%, 90% or at least about 95% is present in a denatured state.

In various embodiments, the whey protein in a denatured state may comprise microparticles having a volume weighted mean diameter D[4,3] of less than about 10, 9.5, 9, 8.5, 8, 7.5, 7, 6.5, 6, 5.5, 5, 4.5, 4, 3.5, 3, 2.5, or 2 μm. In various preferred embodiments, the volume weighted mean diameter D[4,3] may be less than about 5 μm, or less than about 3 μm, or less than about 2 μm. Preferably the volume weighted mean diameter D[4,3] is less than about 10 μm, or less than about 5 μm, or less than about 3 μm, or less than about 2 μm.

In various embodiments the whey protein may be non-hydrolysed. In various embodiments the whey protein may have a degree of hydrolysis of less than about 5%, 4.75%, 4.5%, 4.25%, 4%, 3.75%, 3.5%, 3.25%, 3%, 2.75%, 2.5%, 2.25%, 2%, 1.75%, 1.5%, 1.25%, 1%, 0.75%, or less than about 0.5%. In various preferred embodiments, the whey protein may have a degree of hydrolysis of less than about 4%.

In certain embodiments the whey protein is provided by a whey protein concentrate (WPC), a whey protein isolate (WPI), or a blend of whey protein sources including a blend of WPCs or WPIs or both. In some embodiments the whey protein is provided by a WPC, WPI or a blend thereof, and an ingredient that comprises whey protein and non-whey protein, for example, casein. In one embodiment the ingredient that comprises whey protein and non-whey protein is selected from the group comprising a milk protein concentrate (MPC); total milk protein (TMP); a milk co-precipitate; a micellar casein concentrate (MCC); a milk protein isolate (MPI); proteins of liquid condensed milk; skim milk; skim milk powder; condensed skim milk; whole milk; whole milk powder; or a combination of any two or more thereof.

In one embodiment, the whey protein is provided by an ingredient that comprises a protein content of 35% to 95% by weight of the dry matter of the ingredient.

In certain embodiments, the whey protein ingredient comprises at least about 35%, 50%, 65%, 70%, 75%, or at least about 80% by weight protein. In certain embodiments, higher protein content compositions are utilised, for example the whey protein ingredient comprises at least about 85%, 90%, or at least about 95% by weight protein.

In various embodiments the composition comprises a whey protein ingredient, for example, a WPC or WPI, that has been treated to reduce lactose concentration. In various embodiments the whey protein ingredient comprises less than about 10, 9, 8, 7, 6, 5, 4, 3, 2, 1, 0.5 or less than about 0.1% lactose.

In various embodiments the composition comprises at least about 2, 3, 4, 5, 6, 7, 8, 9, 10, 11, 12, 13, 14, 15, 16, 17, 18, 19 or at least about 20 g whey protein per 100 mL of the composition, and various ranges may be selected from between any of these values, for example, from about 2 to about 20, 4 to about 20, about 5 to about 20, about 6 to about 20, about 7 to about 20, about 2 to about 15, about 4 to about 15, about 5 to about 15, about 6 to about 15 or about 7 to about 15 g whey protein per 100 mL of the composition.

In various embodiments whey protein comprises at least about 1, 2, 5, 10, 15, 20, 25, 30, 35, 40, 45, 50, 55, 60, 65, 70, 75, 80, 85, 90 or at least about 95% by weight of the total protein in the composition, and various ranges may be selected from between any of these values, for example, from about 1% to about 99%, 10% to about 95%, about 20 to about 80%, about 35 to about 80%, about 40% to about 95% or from about 40% to about 80% by weight of the total protein in the composition.

In one embodiment the casein comprises or is provided by an ingredient that comprises soluble casein. In various embodiments the casein is micellar casein, non-micellar casein, or micellar and non-micellar casein.

In various embodiments the casein comprises or is provided by an ingredient comprising milk protein isolate (MPI); milk protein concentrate (MPC); micellar casein isolate (MCI); micellar casein concentrate (MCC); proteins of liquid condensed milk; skim milk; skim milk powder; condensed skim milk; whole milk; whole milk powder; a caseinate; total milk protein (TMP); milk co-precipitates; an MPC or MPI that has been modified to dissociate casein micelles; calcium-chelated casein micelles; a charge-modified casein; a casein ingredient, such as an MPC or MPI, where at least a portion of the calcium or phosphate or both the calcium and phosphate has been replaced with sodium, potassium, zinc, magnesium, or a combination of any two or more thereof; a glycosylated casein or a combination of any two or more thereof.

In various embodiments the casein may comprise or be provided by a casein ingredient such as an MPC or MPI, where at least a portion of the calcium or phosphate or both the calcium and phosphate has been replaced with sodium, potassium, zinc, magnesium, or a combination of any two or more thereof.

In various embodiments the caseinate comprises sodium caseinate, calcium caseinate, magnesium caseinate, potassium caseinate or a combination of any two or more thereof.

In various embodiments the composition comprises a casein ingredient, for example, a MPC or MPI, that has been treated to reduce lactose concentration. In various embodiments the casein ingredient comprises less than about 10, 9, 8, 7, 6, 5, 4, 3, 2, 1, 0.5 or less than about 0.1% lactose.

In various embodiments casein comprises at least about 1%, 5%, 10%, 15%, 20%, 25%, 30%, 35%, 40%, 45%, 50%, 55%, 60%, 65%, 70% or at least about 75% by weight of the total protein in the composition and various ranges can be selected from between these values, for example, from about 1% to about 75%, about 5% to about 75%, about 1% to about 65%, 5% to about 65%, about 10% to about 65%, about 20% to about 65%, about 30% to about 65%, or about 40% to about 65%.

In various embodiments the composition comprises at least about 0, 0.01, 0.1, 1, 2, 3, 4, 5, 6, 7, 8, 9, 10, 11, 12, 13, 14, 15, 16, 17, 18, 19 or at least about 20 g casein per 100 mL of the composition, and various ranges may be selected from between any of these values, for example, from about 0 to about 20, about 0.01 to about 20, 4 to about 20, about 5 to about 20, about 6 to about 20, about 7 to about 20, about 0 to about 15, about 0.01 to about 15 about 4 to about 15, about 5 to about 15, about 6 to about 15 or about 7 to about 15 g casein per 100 mL of the composition.

In one embodiment the casein is non-hydrolysed. In another embodiment the casein is at least partially hydrolysed.

In one embodiment the composition comprises one or more non-dairy proteins. In various embodiments the non-dairy protein comprises algal protein, hydrolysed algal protein, plant protein, hydrolysed plant protein, animal protein, or hydrolysed animal protein, or any combination of any two or more thereof.

In various embodiments the plant protein comprises canola (rapeseed), legume, cereal, nut, or seed protein or any combination of any two or more thereof, optionally wherein any one or more of the plant proteins is a hydrolysed plant protein. In various embodiments the legume protein comprises pea, chickpea, bean, lupin, lentil or soy protein, or any combination of any two or more thereof, optionally wherein any one or more of the plant proteins is a hydrolysed plant protein. In various embodiments the cereal protein comprises rice, wheat, sorghum, maize, corn, or barley protein, or any combination of any two or more thereof, optionally wherein any one or more of the plant proteins is hydrolysed plant protein. In various embodiments the nut protein comprises almond, or cashew protein, or any combination thereof, optionally wherein any one or more of the plant proteins is a hydrolysed plant protein. In various embodiments the seed protein comprises chia, hemp or flax (linseed) protein, or any combination of any two or more thereof, optionally wherein any one or more of the plant proteins is hydrolysed plant protein.

In various embodiments the animal protein may comprise collagen, hydrolysed collagen, recombinant collagen, hydrolysed recombinant collagen, or any combination of any two or more thereof.

In various embodiments the non-dairy protein has a pI of about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9 or about 6, and various ranges can be selected from between these values, for example, from about 3 to about 6, about 3.5 to about 6, about 4 to about 6, about 3 to about 5.5, about 3.5 to about 5.5, about 4 to about 5.5, about 3 to about 5, about 3.5 to about 5 or about 4 to about 5.

In various embodiments, the composition comprises at least about 0, 0.01, 0.1, 0.5, 1, 2, 3, 4, 5, 6, 7, 8, 9, 10, 15, 20, 25 or at least about 30 g non-dairy protein per 100 mL of the composition, and various ranges can be selected from between these values, for example, from about 0 to about 30, about 0.01 to about 30, about 1 to about 30, about 0 to about 20, 0.01 to about 20, about 0.1 to about 20, about 0.5 to about 20, about 0.1 to about 15, about 1 to about 20, about 2 to about 20, about 3 to about 20, about 5 to about 20, about 0 to about 10, about 0.01 to about 10, about 1 to about 10 g non-dairy protein per 100 mL of the composition.

In various embodiments, the composition comprises at least about 0.01, 0.1, 0.5, 1, 2, 3, 4, 5, 6, 7, 8, 9, 10, 15, 20, 25 or at least about 30 g lipid per 100 mL of the composition, and various ranges can be selected from between these values, for example, from about 0.01 to about 30, about 0.1 to about 30, about 1 to about 30, about 0.01 to about 25, about 0.1 to about 25, about 1 to about 25, about 0.01 to about 20, about 0.1 to about 20, about 0.5 to about 20, about 1 to about 20, about 2 to about 20, about 3 to about 20, about 5 to about 20 g about 0.01 to about 15, about 0.1 to about 15, about 1 to about 15, about 2 to about 15, about 5 to about 15, about 0.01 to about 10, about 0.1 to about 10, about 1 to about 10, or about 2 to about 10 g lipid per 100 mL of the composition.

In various embodiments, the composition comprises at least about 0.01, 0.1, 0.5, 1, 2, 3, 4, 5, 6, 7, 8, 9, 10, 15, 20, 25, 30, 35, 40 or at least about 45 g carbohydrate per 100 mL of the composition, and various ranges can be selected from between these values, for example, from about 0.01 to about 4, about 0.01 to about 45, about 0.1 to about 45, about 1 to about 45, about 4 to about 45, about 5 to about 45, about 0.01 to about 40, about 0.1 to about 40, about 1 to about 40, about 4 to about 40, about 5 to about 40, about 0.01 to about 30, about 1 to about 30, about 1 to about 30, about 4 to about 30, about 5 to about 30, 0.01 to about 20, about 0.1 to about 20, about 0.5 to about 20, about 0.1 to about 15, about 1 to about 20, about 2 to about 20, about 3 to about 20, about 4 to about 20, or about 5 to about 20 g carbohydrate per 100 mL of the composition.

In various embodiments the carbohydrate comprises digestible carbohydrate, non-digestible carbohydrate or a combination thereof.

In various embodiments the composition has an energy density of at least about 25, 50, 75, 100, 125, 150, 200, 250, 300, 350 or at least about 400 kcal per 100 mL, and various ranges can be selected from between these values, for example, from about 25 to about 400, 50 to about 400, about 100 to about 400, about 150 to about 400, about 175 to about 400, about 50 to about 350, about 50 to about 300, about 100 to about 300, about 25 to about 300, about 50 to about 300, about 100 to about 300, about 25 to about 250, about 50 to about 250, about 100 to about 250, about 25 to about 200, about 50 to about 200, or about 100 to about 200 kcal per 100 mL of the composition. In various preferred embodiments the composition has an energy density of at least about 200 kcal per 100 mL of the composition.

In various embodiments, the composition comprises, consists essentially of, or consists of 0 g or about or less than about 0.5, 1, 2, 3, 4, or 5 g per 100 mL of the composition of di-, oligo-, and/or poly-saccharides that comprise one glucose unit or no glucose units. Various ranges can be selected from between these values, for example, from about 0 to about 5, about 0 to about 4, or about 0.01 to about 4 g per 100 mL of the composition.

In various embodiments, the composition comprises at least about 0, 0.01, 0.025, 0.05, 0.075, 0.1, 0.15, 0.2, 0.25, 0.3, 0.35, 0.4, 0.45, or 0.5 g emulsifier and/or surfactant per 100 mL of the composition, and various ranges can be selected from between these values, for example, from about 0 to about 0.5, about 0.01 to about 3, or about 0.01 to about 0.2 g per 100 mL of the composition.

In various embodiments, the composition comprises at least about 0.001, 0.002, 0.003, 0.004, 0.005, 0.006, 0.007, 0.008, 0.009, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, or 0.1 g of emulsifier per g of lipid, and various ranges can be selected from between these values, for example, about 0.001 to about 0.1, about 0.002 to about 0.08, or about 0.003 to about 0.06 g per g of lipid.

In various embodiments the composition has a viscosity of less than about 500, 450, 400, 300, 200, 150, 100, 80, 60, 50, 40, 30, or less than about 20 mPa·s when measured at a temperature of 20° C. and a shear rate of 100 s$^{-1}$.

In one embodiment the composition exhibits essentially no gelation or aggregation.

In various embodiments the composition has an average particle size of less than about 20, 18, 15, 12, 10, 9, 8, 7, 6, 5, 4, 3, 2.5, 2, 1.5, 1, 0.9, 0.8, 0.7 0.6, 0.5, 0.4, 0.3 or 0.25 μm as categorised by the surface weighted average particle size parameter d[3,2] and/or the volume weighted mean diameter D[4,3], and useful ranges may be selected between any of these values, for example about 0.25 to about 20, about 0.25 to about 15, about 0.25 to about 10, about 0.25 to about 8, about 0.25 to about 6, or about 0.25 to about 4 μm.

In various embodiments the composition may comprise, consist essentially of, or consist of a total amount of monovalent metal ions of at least about 5, 6, 7, 8, 9, 10, 11, 12, 13, 14, 15, 16, 17, 18, 19, 20, 25, 30, 35, 40, 45, or 50 mg/g of protein, and useful ranges may be selected between these values, for example, about 8 to about 20, about 8 to about 30, about 8 to about 40, about 8 to about 50, about 10 to about 50, about 15 to about 50, about 20 to about 50 and about 50 to about 50 mg/g of protein. In various embodiments the monovalent metal ions may comprise sodium ions, potassium ions, or both.

In various embodiments the composition may comprise, consist essentially of, or consist of an amount of monovalent metal ions of at least about 50, 60, 70, 80, 90, 100, 110, 120, 130, 140, 150, 160, 170, 180, 190, 200, 225, 250, 275, 300, 325, 350, 375, 400, 425, 450, 475, or 500 mg/100 ml of the composition, and useful ranges may be selected between any of these values, for example, from about 50 to about 500, about 100 to about 400, about 150 to about 350, or about 100 to about 500 mg/100 ml.

In various embodiments the composition may comprise, consist essentially of, or consist of an amount of calcium of at least about 50, 60, 70, 80, 90, 100, 110, 120, 130, 140, 150, 160, 170, 180, 190, 200, 225, 250, 275, 300, 325, 350, 375, 400, 425, 450, 475, or 500 mg calcium/100 ml of the composition, and useful ranges may be selected between any of these values, for example, from about 50 to about 500, about 100 to about 400, about 150 to about 350, or about 100 to about 500 mg/100 ml.

In various embodiments the protein in the composition remains soluble in the upper gastrointestinal tract, remains soluble in upper gastrointestinal fluid, does not form a coagulum in the upper gastrointestinal tract or does not form a coagulum in upper gastrointestinal fluid.

In various embodiments the protein in the composition remains soluble or does not form a coagulum at a pH of about 1, 2, 3, 4 or about pH 5. In one embodiment the protein in the composition remains soluble or does not form a coagulum when simulated gastric fluid is added to the composition, for example, simulated gastric fluid prepared as described herein in the Examples (comprising hydrochloric acid, a protease, and a lipase, preferably comprising hydrochloric acid, pepsin, and lipase A, more preferably 1 M hydrochloric acid, pepsin 16 mg/mL, and lipase A 2 mg/mL). In various embodiments, the volume weighted mean diameter D[4,3] and/or the surface weighted mean diameter D[3,2] of protein microparticles in the composition remains less than about 10 µm, or less than about 5 µm, or less than about 3 µm, or less than about 2 µm over a 220 minute period at a pH less than about 4, preferably in the presence of the simulated gastric fluid.

In various embodiments the composition has a viscosity of less than about 500, 450, 400, 300, 200, 150, 100, 80, 60, 50, 40, 30 or less than about 20 mPa·s when measured at a temperature of 20° C. and a shear rate of 100 s$^{-1}$ after storage for at least 2 months, 3 months, 6 months or at least 12 months storage at a temperature of 20, 22 or 25° C.

In various embodiments the viscosity of the composition increases by less than about 10, 20, 30, 40, 50, 60, 70, 80, 90 or less than about 100% when measured at a temperature of 20° C. and a shear rate of 100 s$^{-1}$ after storage for at least 2 months, 3 months, 6 months or 12 months at a temperature of 20, 22 or 25° C.

In various embodiments the composition exhibits no observable gelation, or no observable aggregation, no observable sedimentation or a combination of any two or more thereof, for at least 2 months, 3 months, 6 months or at least 12 months at a temperature of 20, 22 or 25° C.

In various embodiments, the composition may be subjected to a heat treatment having an $F_0$-value of at least 3, 4, 5, 6, 7, 8, 9, 10, 11, 12, 13, 14, 15, 16, 17, 18, 19, 20, 25, 30, 35, or 40 (and half-unit increments thereof, e.g. 19.5), and useful ranges can be selected between these values, for example, 3 to 20, 3 to 30, 3 to 40, 10 to 20, 10 to 30, or 10 to 40.

In various embodiments, when subjected to a heat treatment having an $F_0$-value of at least 3, for example, 121.1° C. for 3 min, 130° C. for 25 s, 135° C. for 7.5 s, 140° C. for 2.5 s, 145° C. for 0.75 s, or 150° C. for 0.25 s, the composition
  a) exhibits substantially no gelation, aggregation or sedimentation
  b) has a viscosity of less than about 500 mPa·s when measured at a temperature of 20° C. and a shear rate of 100 s$^{-1}$,
  c) has an average particle size of less than about 20, 18, 15, 12, 10, 9, 8, 7, 6, 5, 4, 3, 2.5, 2, 1.5, 1, 0.9, 0.8, 0.7, 0.6, 0.5, 0.4, 0.3 or 0.25 µm as categorised by the volume weighted mean diameter D[4,3] and/or the surface weighted average particle size parameter d[3,2], or
  d) a combination of any two or more of a) to c) above.

In one embodiment the heat-treated liquid nutritional composition
  a) has a viscosity of less than about 500 mPa·s when measured at 20° C. and shear rate of 100 s$^{-1}$, or
  b) has an average particle size of less than about 20 µm as categorised by the volume weighted mean diameter D[4,3] and/or the surface weighted average particle size parameter d[3,2], or
  c) exhibits essentially no observable gelation or aggregation or sedimentation, or
  d) any combination of any two or more of (a) to (c) above.

In one embodiment the heat treatment has an $F_0$ value of at least 3. In various embodiments the heat treatment has an $F_0$ value of at least equivalent to 121.1° C. for 3 min, 130° C. for 25 s, 140° C. for 2.5 s or 150° C. for 0.25 s. In one embodiment the heat treatment is sufficient to provide a shelf stable product.

In various embodiments the method comprises heat treating the liquid composition at a temperature of at least about 121, 125, 130, 135, 136, 137, 138, 139, 140, 141, 142, 143, 144, 145, 146, 147, 148, 149 or at least about 150° C. for a period of at least about 0.1, 0.5, 1, 2, 3, 4, 5, 6, 7, 8, 9, 10, 12, 15, 20, 30, 40, 50, 60 seconds or at least about 1, 2, 3, 4, 5, 6, 7, 8, 9 or at least about 10 minutes. Various ranges can be selected from between any of these values, for example, in various embodiments the method comprises heat treating the liquid composition at a temperature of at least about, 121 to about 150, 125 to about 150, 130 to about 150, 135 to about 150, 138 to about 150, 121 to about 145, 125 to about 145, 130 to about 145, 135 to about 145, or about 138 to about 145° C. for at least about 0.1 s to about 10 minutes, about 0.1 s to about 1 minute, about 0.1 s to about 30 s, about 0.5 s to about 30 s, about 1 s to about 30 s, about 3 s to about 30 s about 0.1 s to about 20 s, about 0.5 to about 20 s, about 1 to about 20 s, about 3 to about 20 s, about 0.1 to about 10 s, about 1 to about 10 s, about 3 to about 10 s, about 0.1 to about 7 s, about 1 to about 7 s, about 3 to about 7 s, about 0.1 to about 5 s, about 1 to about 5 s or about 3 s to about 5 s.

In one embodiment the heat treatment is an indirect heat treatment. In another embodiment the heat treatment is a direct heat treatment.

In one embodiment, the liquid composition has a pH of greater than 6.0, 6.5, 7.0, or 7.5 when heat treated.

In one embodiment the method further comprises drying the heat-treated liquid composition.

In one exemplary embodiment, prior to packaging or consumption the heat-treated liquid composition undergoes no further heat treatment. In one exemplary embodiment, prior to packaging or consumption the heat-treated liquid composition undergoes no further sterilisation. In one exemplary embodiment, prior to packaging or consumption no further ingredients are added to the heat-treated liquid composition, such that its composition is unchanged.

In one embodiment, the method further comprises aseptic handling, bottling and/or packaging the heat-treated liquid composition.

In various embodiments, the person in need of nutrition may be suffering from or predisposed to a disease or condition, or may be being or have been treated for a disease or condition, is an elderly person, a person that is recovering from a disease or condition, or a person that is malnourished.

In other embodiments, the person may also be a healthy person, such as a sportsperson or active elderly, including persons having particular nutritional requirements.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

BRIEF DESCRIPTION OF THE DRAWINGS

The invention will now be described by way of example only and with reference to the drawings in which.

DETAILED DESCRIPTION OF THE INVENTION

Figure 1:
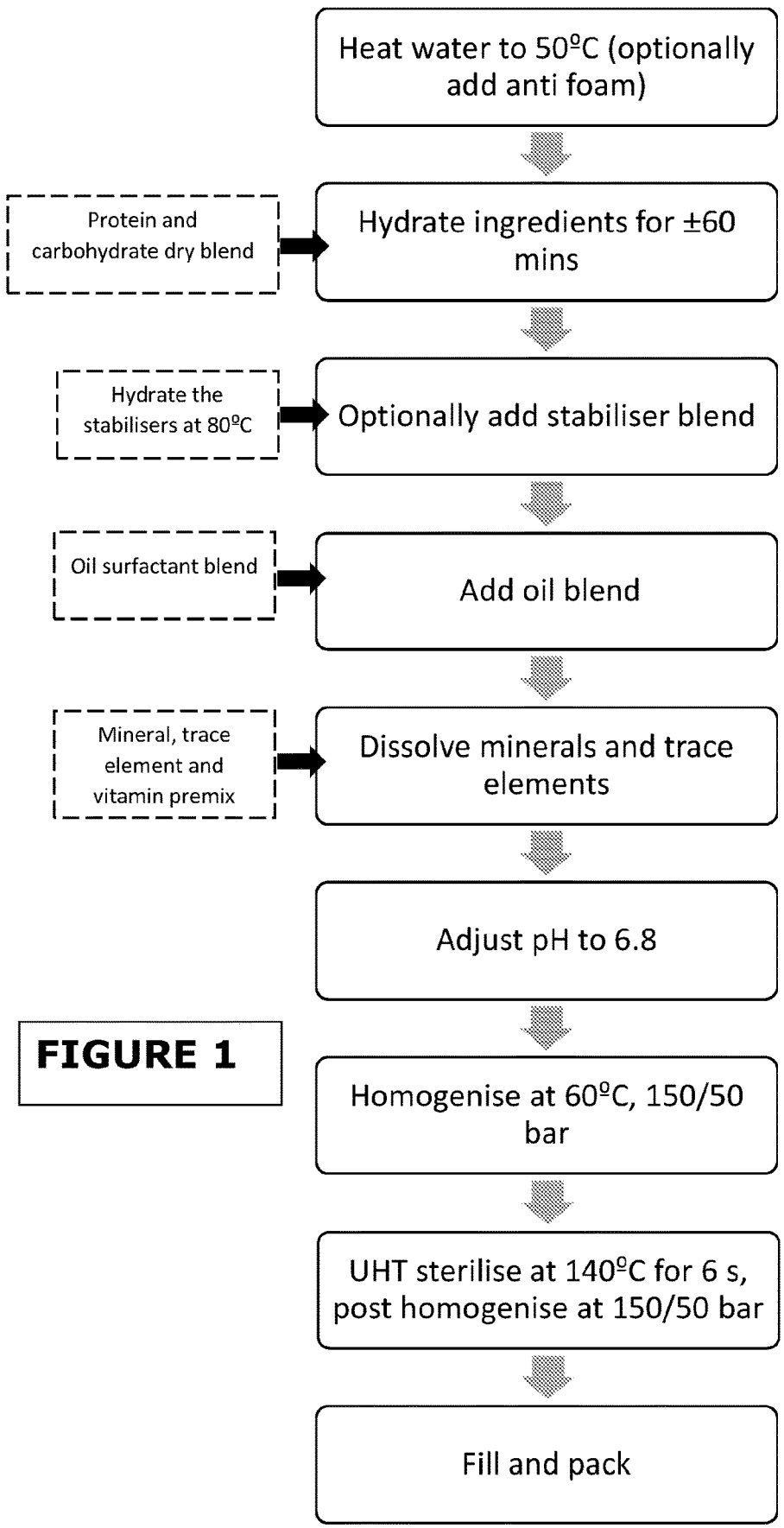
FIG. 1 is a flow chart showing an exemplary method of manufacturing the liquid nutritional compositions described herein.

The present invention provides heat-treated, shelf stable, high protein liquid nutritional compositions of neutral pH comprising both whey protein and non-whey protein. Surprisingly, the inventors have found that by combining whey protein with a second protein source comprising casein and/or one or more non-dairy proteins, high protein (in particular, high whey protein) liquid nutritional compositions of neutral pH are produced that are stable to the high temperature heat treatment necessary to provide shelf stability and microbial control. In various embodiments, the liquid nutritional compositions remain soluble at low pH such that digestive coagulation is controlled following consumption and coagulum formation in the upper gastrointestinal tract is reduced or eliminated. Advantageously, in various embodiments the high protein liquid nutritional compositions described herein have low viscosity compared with equivalent high protein liquid compositions comprising non-hydrolysed casein as the main or sole source of protein. Low viscosity of liquid nutritional compositions is desirable for ease of administration and consumption.

1. Definitions

The phrase "calcium depleted" is used herein to refer to a casein composition, such as a milk protein concentrate (MPC), in which the concentration of calcium bound to casein has been reduced and is lower than the concentration of calcium bound to casein in the corresponding non-depleted composition. Such a composition may also be depleted in other divalent cations, and so have a lower concentration of divalent cations bound to casein, for example, magnesium, than the corresponding non-depleted composition. Similarly, reference to calcium in casein protein is a reference to bound calcium—that is, calcium bound by the casein protein.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

An "effective amount" is the amount required to confer therapeutic effect. The interrelationship of dosages for animals and humans (based on milligrams per meter squared of body surface) is described by Freireich, et al., 1966. (see Freireich E J, Gehan E A, Rall D P, Schmidt L H, Skipper H E (1966) Quantitative comparison of toxicity to anticancer agents in mouse, rat, hamster, dog, monkey and man. Cancer Chemother Rep 50: 219-244). Body surface area can be approximately determined from height and weight of the subject. See, e.g., Scientific Tables, Geigy Pharmaceuticals, Ardley, New York, 1970, 537. Effective doses also vary, as recognized by those skilled in the art, dependent on route of administration, carrier usage, and the like.

The term "liquid nutritional composition" refers to an aqueous composition to be administered preferably by mouth or by other means, generally by tube feeding, to the stomach of a patient. Such other means include naso-gastric feeding and gastric feeding. Liquid nutritional compositions include "medical foods", "enteral nutrition", "food for special medical purposes", liquid meal replacers and supplements. The liquid nutritional compositions of the present invention provide significant amounts of protein and carbohydrate and usually also lipid. They may also include vitamins and minerals. In exemplary embodiments they provide balanced meals.

The term "milk protein concentrate" (or MPC) is a milk protein product in which greater than 55%, preferably greater than 75% of the dry matter is milk protein and the ratio of casein to whey proteins is approximately that of milk. Such concentrates are known in the art.

The phrase "maintaining or increasing muscle mass" and its grammatical equivalents and derivatives, refers to an increase in muscle protein synthesis and/or a decrease in muscle protein breakdown which results in a gain or maintained muscle mass.

As used herein, "non-dairy protein" includes any protein that is not a milk protein, i.e. any protein that is not derived from animal milk. Non-dairy protein includes plant-derived protein and algal protein.

As used herein, "non-whey protein" when used with reference to a protein-containing composition, includes any protein that is not whey protein. Non-whey protein useful in the compositions described herein includes casein and protein derived from one or more non-dairy sources.

The phrase "preventing or reducing loss of muscle mass" and its grammatical equivalents and derivatives, refers to prevention or decrease in muscle protein breakdown resulting in maintained muscle mass or decreased rate of muscle loss.

The term "shelf-stable" as used herein in relation to liquid nutritional compositions refers to compositions that remain in a liquid state in which essentially no sedimentation, gelation or aggregation is observed and negligible bacterial growth occurs when packaged aseptically after prolonged storage at a temperature of about 20° C., 22° C. or about 25° C. for at least about 2 months, 3 months, about 6 months or at least about 12 months.

A "subject" refers to a vertebrate that is a mammal, for example, a human. Mammals include, but are not limited to, humans, farm animals, sport animals, pets, primates, mice and rats.

Unless indicated otherwise, the whey protein and non-whey protein for use herein is substantially non-hydrolysed.

The term "substantially non-hydrolysed" as used herein includes protein that is not hydrolysed (intact) and protein having a degree of hydrolysis of less than about 4%, 3.75%, 3.5%, 3.25% 3%, 2.75%, 2.5%, 2.25%, 2%, 1.75%, 1.5%, 1.25%, 1%, 0.75%, or less than about 0.5%.

The term "whey protein concentrate (WPC)" as used herein refers to a fraction of whey from which lactose has been at least partially removed to increase the protein content to at least 20% by weight. In certain embodiments, the WPC has at least 35%, at least 40%, at least 55%, at least 65%, and in certain embodiments at least 80% by weight of the total solids (TS) as whey protein. In some examples, the proportions of the whey proteins are substantially unaltered relative to those of the whey from which the WPC is derived. In one embodiment, the WPC is an evaporated whey protein retentate. For the purposes of this specification, the term "WPC" includes whey protein isolates (WPI) when the context allows.

The term "whey protein isolate" as used herein refers to a composition that consists primarily of whey proteins with negligible lipid and lactose content. Accordingly, the preparation of WPI typically requires a more rigorous separation process such as a combination of micro filtration and ultra-filtration or ion exchange chromatography. It is generally recognised that a WPI refers to a composition in which at least 90 weight % of the solids are whey proteins.

Particularly contemplated whey protein ingredients include WPIs and WPCs having at least 90% of the TS as whey protein.

2. Liquid Nutritional Compositions

The liquid nutritional compositions may also comprise a wide variety of vitamins and minerals required to sustain patients nutritionally for long periods of time, and minor components such as antioxidants, flavouring and colouring. The amounts of vitamins and minerals to be used in certain embodiments are those typical of meal replacement products known to those skilled in the art. The micro-nutritional requirements of various sub-groups of the population are also known. The recommended daily requirements of vitamins and minerals can be specified for various population subgroups. See for instance, Dietary Reference Intakes: RDA and AI for vitamins and elements, United States National Academy of Sciences, Institute of Medicine, Food and Nutrition Board (2010) tables recommended intakes for infants 0-6, 6-12 months, children 1-3, and 4-8 years, adults males (6 age classes), females (6 age classes), pregnant (3 age classes) and lactating (3 age classes). Concentrations of essential nutrients in the liquid nutritional composition can be tailored in the exemplary serve size for a particular subgroup or medical condition or application so that the nutrition and ease of delivery requirements can be met simultaneously.

For instance, the level of added minerals can be selected based on European Commission guideline on Food for Special Medical Purposes (FSMP) directive. One can choose to add higher levels for specific nutritional reasons. Examples of compositions of the invention having very good heat stability at pH from about 6 to 8 in the presence of various amounts of minerals.

In one embodiment the composition comprises at least about 10, 20, 25, 30, 40, 50, 60, 70, 75, 80, 90 or 100% of the recommended daily intake (RDI) of vitamins and minerals as set by European (FSMP) or USDRA regulations in a 100 mL, 250 mL, 500 mL or 1 litre portion.

The lipid used may be vegetable lipid or animal lipid, including dairy lipid and fish oils. Vegetable oils are often exemplary because of their ease of formulation and lower saturated fatty acid content. Exemplary vegetable oils include canola (rapeseed) oil, corn oil, sunflower oil, olive or soybean oil.

In various embodiments the composition comprises stabilisers or emulsifiers. Useful emulsifiers for stabilising the lipid droplets include lecithins, mono and diglycerides, polyglycerol esters, milk phospholipids, citric acid esters (citrems), and datems. These emulsifiers can be added in an amount of about 0.003 g to about 0.06 g per gram of lipid. Useful stabilisers include carrageenan, gellan gum, pectin, guar gum, locust bean gum, carboxymethyl cellulose and microcrystalline cellulose and combinations thereof. Those of skill in the art will recognise that many different gum forms, in addition to those listed above are suitable for use in the compositions disclosed herein.

The carbohydrate used typically comprises digestible carbohydrate as 75-100% of the carbohydrate. The carbohydrate may comprise monosaccharides, disaccharides, oligosaccharides and polysaccharides and mixtures thereof. Oligosaccharides of glucose are typically used. A number of these are commercially available as maltodextrin (3-20 DE) or corn syrup for the shorter chain carbohydrates (>20 DE). Non-digestible carbohydrates may also be included, for example, fructooligosaccharides, inulin, and galactooligosaccharides. These are typically present in amounts of 0.2-5%, preferably 0.2-4% of the composition. Fibre, including insoluble fibre, can also be included.

In one embodiment the composition may additionally comprise a source of amino acids, amino acid precursors or amino acid metabolites or any combination of any two or more thereof, preferably free amino acids, amino acid precursors or amino acid metabolites.

In various embodiments the protein ingredients are provided in liquid or dry (powder) form, or a blend thereof.

The total protein in the composition is the sum of all protein contributed by all protein-containing ingredients in the composition. The amount of whey protein in the composition is the sum of the whey protein contributed by all whey protein-containing ingredients in the composition. For example, in embodiments where the composition comprises a WPC or WPI (such as a heat denatured WPC or WPI) and an ingredient comprising both whey and casein (such as an MPC), the total whey protein in the composition is the sum of the total whey protein present in the WPC and/or WPI and the MPC.

One or more of the protein ingredients, for example the WPC, WPI, or casein ingredient, or the liquid nutritional composition may be treated to reduce lactose content. In various embodiments the protein ingredient or liquid nutritional composition is treated with an enzyme such as beta-galactosidase, or subjected to filtration to remove lactose. Suitable enzyme treatments and filtration protocols to reduce lactose content will be apparent to those skilled in the art.

In various embodiments the composition comprises less than about 10, 9, 8, 7, 6, 5, 4, 3, 2, 1, 0.5 or less than about 0.1% lactose.

Whey

Exemplary whey protein for use in the invention includes whey protein concentrates and whey protein isolates. Whey protein is recognised as a complete protein known for its excellent amino acid profile which provides all the essential amino acids and has high cysteine and leucine content. Whey protein is also known for its ease of digestion.

WPC is rich in whey proteins, but also contains other components such as lipid, lactose, and, in the case of cheese whey-based WPCs, glycomacropeptide (GMP), a casein-related non-globular protein that is non-denaturable. Typical methods of production of whey protein concentrate utilise membrane filtration, and alternative methods of production of WPC particularly suited to application in the present invention are described herein.

Whey proteins may originate from any mammalian animal species, such as, for instance cows, sheep, goats, horses, buffalos, and camels. Preferably, the whey protein is bovine.

Exemplary methods for preparing WPCs suitable for use in the present invention are provided in PCT International Application PCT/NZ2007/000059 (published as WO 2007/108709) and PCT/NZ2010/000072 (published as WO 2010/120199) and PCT International Application PCT/IB2012/056103 (published as WO2013/065014), each incorporated by reference herein in their entirety.

In various embodiments, whey protein may be prepared by a method comprising
a) providing an aqueous WPC or WPI solution having a protein concentration of about 15-50% (w/v) at a pH of about 4.7-8.5, and
b) subjecting the solution to a heat treatment by heating the solution to more than about 50° C. for a time that allows protein denaturation to occur while under conditions of turbulent flow, for example with a Reynolds number of at least about 500.

Heat treatment is applied in the preparation of the protein, such as the WPC, to impart the required denaturation and to ensure it is suspendable. Whey protein comprises high levels of globular proteins that are sensitive to aggregation in the denatured state. The denaturation temperature of β-lactoglobulin is pH-dependent, and at pH 6.7 irreversible denaturation occurs when the protein is heated above 65° C. This denaturation is believed to expose a free thiol group, which is reported to initiate inter-protein disulfide bond formation leading to polymerization resulting in aggregate formation. Other disulfide bridges and cysteine residues are thought to play a role in the polymerization reaction. α-lactalbumin also has a denaturation temperature of about 65° C.

One exemplary method of producing substantially denatured whey proteins is called microparticulation. Microparticulation is generally achieved by thermal aggregation or acid precipitation, often combined with high shear and high pressure conditions (Havea, Baldwin, & Carr, 2009). Microparticulated whey protein can be regarded as a combination of native proteins and both soluble and insoluble protein aggregates of controlled size. The aggregated particles have limited interaction with each other, because free thiol groups are reduced during microparticulation. Thus, one of the key parameters that relate to the functional properties of microparticulated whey protein is the extent of protein denaturation in the product.

The size, shape and density of the protein aggregates are influenced by a number of environmental and processing parameters including temperature, heating rate, pressure, shear, pH and ionic strength. Depending on the combination of these parameters, the aggregates may form compact micro-particles having a volume weighted mean diameter D[4,3] and/or a surface weighted mean diameter D[3,2] of less than about 10 μm. For example, microparticulated whey can be formed under specific ionic strength and shear conditions. These particles have a compact structure, a low intrinsic viscosity and a low specific volume. Further, it is known that a relationship exists between aggregates size and heating temperature for microparticulated whey produced under shear conditions.

The whey protein may be prepared from a mixture of WPCs, or from a mixture of proteins. In various embodiments, the protein is or comprises a whey protein concentrate (WPC) or whey protein isolate (WPI).

In some embodiments the whey protein in the composition is provided by a blend of a WPC and/or WPI and one or more ingredients comprising whey and non-whey protein. For example, in one embodiment the whey protein is provided by a WPC and/or WPI and an MPC.

In certain embodiments, the whey protein ingredient is made according to a process as specified according to U.S. Pat. No. 6,767,575 (Huss & Spiegel), US2006/0204643 (Merrill et al), U.S. Pat. No. 4,734,827 (Singer et al), U.S. Pat. No. 5,494,696 (Holst et al), PCT/NZ2010/000072 (published as WO 2010/120199), EP0412590 and EP0347237 (Unilever). Each method of making a whey protein ingredient would impart different properties so anyone using this invention should select the protein ingredient to best suit their process.

In certain embodiments, the whey protein ingredient is a heat-treated, substantially denatured whey protein, for example the WPC or WPI, is dried and then rehydrated in the composition or in an aqueous component of it. In certain embodiments, the heat-treated, substantially denatured WPC has at least 35%, at least 55% (on a moisture and fat-free basis), for example at least 70% protein and in certain embodiments at least 80% protein.

The heat treated, substantially denatured liquid WPCs (without drying) may also be used with the same protein concentration characteristics as defined for the dried ingredient.

In certain embodiments the heat treated, substantially denatured whey protein, for example the WPC or WPI, is dried to a moisture content of less than 5%, or a water activity level that facilitates storage of the dry ingredient for several months without undue deterioration.

In certain exemplary embodiments, the whey protein source is available as a powder, preferably a WPC or WPI powder.

In certain embodiments the heat-treated or denatured protein, for example the WPC, comprises less than 90% by weight protein. For example, the heat-treated or denatured protein comprises at least 51% by weight protein, in certain embodiments at least 70%, in certain embodiments at least 80% protein, wherein at least 55% of the total denaturable protein is present in a denatured state.

In certain embodiments the heat-treated or denatured protein, for example the WPC, has a volume weighted mean diameter D[4,3] and/or a surface weighted mean diameter D[3,2] of less than about 10 µm. In various embodiments, the whey protein in a denatured state may comprise microparticles having a volume weighted mean diameter D[4,3] and/or a surface weighted mean diameter D[3,2] of less than about 10, 9.5, 9, 8.5, 8, 7.5, 7, 6.5, 6, 5.5, 5, 4.5, 4, 3.5, 3, 2.5, or 2 µm. In various preferred embodiments, the volume weighted mean diameter D[4,3] and/or the surface weighted mean diameter D[3,2] may be less than about 5 µm, or less than about 3 µm, or less than about 2 µm.

In various embodiments the composition comprises a whey protein ingredient, for example, a WPC or WPI, that has been treated to reduce lactose concentration. Breakdown of lactose into its monosaccharides galactose and glucose by, for example, enzyme treatment of the protein ingredient, delivers benefits such as increased sweetness, which enables the sugar content of the nutritional composition to be reduced. The use of a low lactose whey ingredient may also result in improved mouthfeel properties such as increased creaminess or mouthcoating.

Casein

Casein for use in any of the compositions described herein includes soluble casein in the form of non-micellar casein, micellar casein, non-micellar caseinate, α-casein, β-casein, kappa-casein, a casein fraction, an alpha-casein fraction, a beta-casein fraction, a kappa-casein fraction, casein treated by ultra high-pressure (UHP) processing, translucent casein or any combination of any two or more thereof.

In various embodiments the casein is micellar casein, non-micellar casein, or micellar and non-micellar casein.

Non-micellar casein results from dissociation of the casein micelle resulting in smaller fractions or soluble caseins. Ingredients that comprise non-micellar casein are well known in the art.

In various embodiments the casein comprises or is provided by an ingredient comprising milk protein isolate (MPI), milk protein concentrate (MPC), micellar casein isolate (MCI), micellar casein concentrate (MCC), proteins of liquid condensed milk, skim milk, condensed skim milk, skim milk powder, whole milk, whole milk powder, a caseinate, total milk protein (TMP), milk co-precipitates, an MPC or MPI that has been modified to dissociate casein micelles, calcium-chelated casein micelles, a charge-modified casein, a casein ingredient, such as an MPC or MPI, where at least a portion of the calcium or phosphate or both the calcium and phosphate has been replaced with sodium, potassium, zinc, magnesium and like, or a combination of any two or more thereof; a glycosylated casein or a combination of any two or more thereof.

In one embodiment the casein comprises casein particles of about 40, 50, 60, 70, 50, 90, 100, 110, 120, 130, 140, 150, 160 or 165 nm in diameter, and useful ranges may be selected between any of these values (for example about 50 to about 165, about 50 to about 100 or about 50 to about 70 nm).

Total milk proteins (TMPs) and milk co-precipitates thereof comprise whey protein and casein and may be prepared using any method known in the art, such as those methods described in U.S. Pat. No. 4,376,072. For example, TMPs suitable for use in the invention may be treated with alkali to solubilise the protein using methods known in the art. Co-precipitates suitable for use in the invention may be produced using methods known in the art such as those described in Hayes et al, 1969 (Australian Journal of Dairy Technology, June 1969). TMPs and co-precipitates comprise whey protein that is in a partially or fully denatured state, and so can provide both casein and the denatured whey protein present in the nutritional compositions described herein.

MPCs are frequently described with the % dry matter as milk protein being appended to "MPC". For example, MPC70 is an MPC with 70% of the dry matter as milk protein. Generally, MPCs are prepared by processes invoking ultrafiltration either to prepare a stream enriched in casein or a stream enriched in whey protein. The streams may be blended to attain desired ratios of casein to whey protein. In another embodiment, the milk protein concentrate may be prepared by blending a stream of skim milk with a stream of whey protein concentrate prepared by ultrafiltration, treating either the skim milk stream or the combined stream by cation exchange and optionally concentrating or drying. Suitable MPCs for use herein may be prepared from a mixture of MPCs.

In one embodiment the casein comprises or is provided by a calcium-depleted casein composition. Examples of suitable calcium-depleted casein compositions for use herein include those prepared by the methods described in published international PCT application WO 2001/041578 and published international PCT application WO 2004/057971, incorporated herein by reference in their entirety.

Calcium-depleted MPCs are MPCs in which the calcium content is lower than the corresponding non-depleted MPC. These products generally also have a lower content of other divalent cations, for example, magnesium, than corresponding non-depleted products. Preferably the calcium-depleted MPC is dried to a moisture content of less than 5%, or a water activity level that facilitates storage of the dry ingredient for several months without undue deterioration. Preferred MPCs for use in the invention have calcium that is manipulated by a cation exchange method. The manufacture and application of these calcium-depleted MPCs have been previously disclosed in U.S. Pat. No. 7,157,108, published PCT application WO2008/026940 and US published patent application 2010/0021595. These documents are fully incorporated herein by reference.

UHP-processed translucent casein is produced by subjecting a casein-containing composition to a high pressure treatment, as described in international patent application WO 2004/091309, incorporated herein by reference in its entirety. Translucent casein may also be produced via cation exchange of skim milk, milk protein concentrate or milk protein isolate using the methods described and exemplified in international patent application WO2001/041579, incorporated herein by reference in its entirety.

The term "caseinate" refers to a chemical compound of casein and a metal ion produced by acid precipitation of casein followed by resolubilisation with alkali comprising the metal ion. Hydroxide solutions comprising sodium, potassium and magnesium ions are used to produce sodium caseinate, potassium or magnesium caseinate. A description of caseinates and methods of producing caseinates suitable for use herein are described in Fox & McSweeney, 2003 and the Dairy Processing Handbook, 2003.

Non-Dairy Protein

In various embodiments the composition comprises one or more, two or more or three or more non-dairy proteins selected from the group comprising algal, plant proteins, and animal proteins, and hydrolysed forms thereof.

Suitable non-dairy proteins for use in the compositions described herein include proteins that are soluble at a pH of about 6 to about 8 or proteins provided in a form that is suspendible in solution. Suitable non-dairy proteins include proteins that are soluble and do not form aggregates under acidic conditions as present in the upper gastrointestinal tract.

In one embodiment the non-dairy protein is at least partially hydrolysed. In another embodiment the non-dairy protein is non-hydrolysed. In one embodiment the composition comprises a blend of two or more non-dairy proteins wherein at least one non-dairy protein is at least partially hydrolysed and at least one non-dairy protein is non-hydrolysed.

In one embodiment the composition comprises soy protein, rice protein or pea protein. In another embodiment the composition comprises soy and pea protein.

3. Properties of the Composition

For the purpose of the present specification, viscosity is measured at 20° C. using a rheometer such as an Anton Paar instrument using a cup and bob assembly at a shear rate of 100 $s^{-1}$, unless otherwise indicated. It will be appreciated that other methods to measure or estimate viscosity are well known in the art and may be employed where appropriate.

For the purpose of the present specification, energy densities are measured by calculation using standard calorific values of food constituents. Again, it will be appreciated that other methods to measure or estimate energy density, such as calorimetry, are well known in the art and may be employed where appropriate.

For the purpose of the present specification, mean particle size (characterised by D[4,3] or D[3,2] or both) is measured using a Malvern Mastersizer 2000 (Malvern Instruments Ltd, Worcs, UK) with a refractive index for the particles of 1.46 for emulsion based beverages and 1.52 for powders in suspension, and for the solvent of 1.33.

Methods for assessing protein concentrations are well-known in the art, for example as measured protein nitrogen by the Kjeldahl method. This method is based on nitrogen determination and protein concentration is calculated by multiplying the total nitrogen result by a conversion factor of 6.38 for dairy proteins.

The degree of hydrolysis of protein as used herein refers to the percentage of peptide bonds present in the protein that are cleaved. The degree of hydrolysis may be determined using methods including but not limited to HPLC, SDS PAGE and reagent-based methods such as the o-phthaldialdehyde (OPA) method. In the OPA method, a thiol reagent, such as OPA, ethanediol or dithiothreitol, or derivatives thereof, are reacted with casein, leading to binding of the thiol reagent to specific amino acids within the hydrolysed protein. Thiol-bound amino acids fluoresce strongly at 450 nm and the level of fluorescence is used as a quantitative measure of the degree of hydrolysis.

Methods to determine the degree of protein denaturation are well known in the art. One exemplary method used herein relies on HPLC (Elgar et al (2000) J Chromatography A, 878, 183-196); and other methods suitable for use include methods reliant on an Agilent 2100 Bioanalyzer (Agilent Technologies, Inc. 2000, 2001-2007, Waldbronn, Germany) and microfluidic chips, and utilising Agilent 2100 Expert software (e.g. Anema, (2009) International Dairy J, 19, 198-204), and polyacrylamide gel electrophoresis (e.g. Patel et al, (2007) Le Lait, 87, 251-268).

Powders may be characterised by measuring the residual denaturable protein as a proportion of total protein (TN× 6.38) according to the following formula:

$$\% \text{ Residual denaturable protein} = \frac{(\text{soluble denaturable protein}) \times 100}{(\text{Total Nitrogen} \times 6.38)}$$

where the soluble whey protein is determined using reverse phase HPLC (Elgar et al., 2000) as described above and is expressed as grams protein/100 grams powder.

The denaturable whey protein is measured as Σ(bovine serum albumin+α-lactalbumin+β-lactoglobulin+lactoferrin+immunoglobulins).

For a cheese WPC80 that has been carefully manufactured, the sum of the above components would typically be 60-63% of the TN and so the proportion of denaturable protein that has been denatured can be estimated according to the following formula:

$$1 - \frac{(\text{residual denaturable protein}) \times 100}{61}$$

Heat stability or shelf stability of the liquid composition includes having no gelation, sedimentation or aggregation either directly after heat treatment or after prolonged storage at temperatures of about 25° C., e.g. at least 2 months, 3 months or preferably at least 6 months or 12 months.

Gelation of a liquid nutritional composition is considered to be a change in state from a liquid to a soft to firm solid. Gelation can be assessed visually and by touch. If the solution no longer flows following heating, it is considered to have gelled.

To attain the required sterility while maintaining liquidity, the proteins must be stable to the heat treatment conditions. The nutritional composition has been found to be surprisingly stable to the required heat treatments in the pH range 6 to 8.

An exemplary method for assessing the heat stability of milk is well known in the art. The method of heat coagulation time (HCT) involves sealing a milk sample (1-2 mL) in a glass tube which is clipped onto a platform and placed in a silicone oil bath thermostatically controlled at 140° C. with a defined rocking rate. The length of time that elapses between placing the container in the oil bath and onset of visible aggregates formation is defined as the HCT (Singh H & Creamer L K (1992), Determination of heat stability, In: Advanced Dairy Chemistry e.d. Fox P F Elsevier). Applicants believe, without wishing to be bound by any theory and based on their experience including that described herein, any liquid nutritional composition having a heat coagulation time of less than 65 s has a high risk of extensive fouling and blocking of UHT heating equipment, while any liquid composition with 65-80 s HCT has a potential risk of fouling. As described herein, liquid nutritional compositions having a heat coagulation time of higher than 80 s is stable to UHT heating treatment at 140° C. for 5 s. Alternatively or additionally, following heating at 121° C. in an oil bath, a sample showing coagulation before 3 minutes has a high risk of gelation and aggregation in a retort can.

The liquid nutritional composition coagulates to a reduced extent or not at all in the upper gastro-intestinal tract or under stomach conditions. Digestion in the stomach starts with the release of low pH stomach fluid. Introduction of proteins in the acidic environment of the stomach can result in the formation of a curd which slows the digestion process and delays gastric emptying.

An exemplary method for assessing the physical characteristics, such as coagulation of the compositions under these conditions is the in vitro acidification method described herein in the examples and in Schnell, 2005 (Nicholas Schnell (2005) Gastric emptying and plasma glucose response in men following ingestion of milk from different species. Massey University, Palmerston North, New Zealand. Available online: "mro.massey.ac.nz". In this method, a simulated gastric fluid (SGF) is prepared and added to a liquid nutritional composition. Gelling of the composition is indicative of coagulation under upper gastrointestinal conditions.

4. Method of Manufacture

An exemplary method for producing liquid nutritional compositions of the invention is described below and shown in FIG. 1. Suitable alterations to the method that achieve the liquid nutritional compositions described herein will be apparent to those skilled in the art.

In one embodiment, the dried non-fat ingredients (protein and carbohydrate dry blend) are dispersed in water, and allowed to hydrate. In one embodiment the ingredients are allowed to hydrate for about 60 minutes. In one embodiment the water is heated to a temperature of approximately 50° C. to aid hydration of the dry ingredients. Optionally, anti-foam is added. In one embodiment a stabiliser blend is added. In one embodiment stabilisers are added to water at 80° C. before being admixed.

The hydrated mixture is then mixed vigorously or emulsified with the lipid ingredients, for example, one or more oils or an oil-surfactant blend. In one embodiment the lipid ingredients are combined with emulsifiers and/or stabilisers.

In one embodiment the sugar (carbohydrate) and protein are mixed to assist in protein dispersion and solubilisation. Whilst protein and sugar (carbohydrate) mixes are the exemplary method of dispersion and solubilisation, protein and lipid mixes can also be used for improved dispersion and solubilisation.

In one embodiment one or more minerals, trace elements and vitamins are added. Suitable mineral, trace elements and vitamin premixes that are known in the art may be used.

The components of the composition of the invention are typically homogenised to reduce the lipid/oil droplet size and form an oil-in-water emulsion, and then heat treated.

The homogenisation step used to form a stabilised food composition involves application of shear forces to reduce droplet or particle size. For some embodiments high shear stirring, for example, in a homogeniser or high shear rotor-stator disperser may be used. In certain embodiments the recombined base of liquid nutritional composition has an average particle size of less than 20 µm as categorised by the surface weighted average particle size parameter D[3,2] and/or the volume weighted mean diameter D[4,3], for example less than 10 µm, even for example less than 2 µm, or in certain embodiments less than 1 µm.

In one embodiment, homogenisation of the nutritional composition is carried out prior to the final heat treatment, or may be conducted as part of the heat treatment, including for example during an initial, partial, pre-heating, or post-heating step. In one exemplary embodiment the composition is homogenised at 60° C. at 150/50 bar. In certain embodiments, for example of the liquid nutritional composition, the composition has after heating, and optionally after blending or homogenisation, a mean surface weighted particle size, D[3,2] and/or a volume weighted mean diameter D[4,3] of from about 0.3 µm to about 2 µm, or from about 0.5 µm to about 1.5 µm. For example, the composition has a mean particle size of about 1, 0.5, 0.4 or about 0.3 µm.

The pH of the composition is adjusted to a pH of from about 6 to about 8 before heat treatment. In one embodiment the pH is adjusted to a pH of from about pH 6 to about pH 8 before homogenisation. In another embodiment the pH is adjusted to a pH of from about pH 6 to about pH 8 after homogenisation.

In various exemplary embodiments, the liquid composition has a mean particle size that does not substantially increase when heated, for example, when heated with a heat treatment with an $F_0$-value of at least equivalent to 121° C. for 3 minutes, for example, when heated at greater than 140° C. for 5 or 6 s. For example, the composition has a mean particle size that does not increase by more than 4-fold when heated at greater than 140° C. for 5 s, in certain examples does not increase by more than 3-fold, by more than 2-fold, when heated with a heat treatment with an $F_0$-value of at least equivalent to 140° C. for 5 s.

In one exemplary embodiment, the liquid composition has a mean particle size that does not increase when heated to a temperature of about 135° C. to about 150° C. for about 0.1 to about 10 s, or about 121° C. to about 135° C. for about 7.5 s to about 3 mins.

The liquid nutritional composition is subjected to heat treatment after it has been prepared to achieve a shelf stable composition, preferably to achieve commercial sterilisation. Commercial sterilisation means the condition achieved by application of heat, sufficient alone or in combination with other appropriate treatments to render the product free of microorganisms capable of growing under normal non-refrigerated conditions at which the product is likely to be held during distribution and storage.

As will be appreciated by those skilled in the art, the lethal effect of high temperatures on microorganisms is dependent on both temperature and holding time, and the reduction in time required to kill the same number of microorganisms as temperature is increased is well known. The time taken to reduce initial microbial numbers, at a specified temperature, by a particular amount, is commonly referred to as a "F value". As described in Mullan, W. M. A. (2007) (Mullan, W. M. A., Calculator for determining the F value of a thermal process. [On-line]. Available from: www.dairy-science.info/calculators-models/134-f-value-thermal-process.html) and references therein, the F value of a thermal process can be calculated by plotting lethal rates against process time, where lethal rate can be calculated using the following equation (Stobo, 1973):

$$\text{Lethal rate} = 10^{(T-Tr)/z}$$

where T is the temperature at which the lethal rate is calculated, Tr is the reference temperature at which the equivalent lethal effect is compared, and z is the reciprocal of the slope of the thermal death curve for the target microorganism or spore (all values in degrees Celsius).

F values can thus be used to describe the thermal input into a particular process. $F_0$ is a measure of the amount of lethal heat which results from a specified thermal process (usually measured at the point of lowest lethality in the container). The number is the lethal effect equivalent to the number of minutes at 121.1° C. when assuming instantaneous heating and cooling and a z value of 10° C. (www.foodsafety.govt.nz) As discussed herein, the liquid nutritional compositions of the present invention are typically subjected to a heat treatment step having an $F_0$-value of at least equivalent to preferably a heat treatment having an $F_0$ value of at least equivalent to 121° C. for 3 min, most preferably a heat treatment having an $F_0$ value of at least equivalent to 140°° C. for 5 s whilst exhibiting useful heat stability, such as not forming a gel.

Various heat treatments of the liquid nutritional composition may be used. Ultra-high temperature (UHT) treatment is exemplary. Typical UHT conditions are 135 to 150° C. for 2 to 18 seconds, but longer durations are possible, for example 10 seconds, 15 seconds, 20 seconds, or more. Another process used to ensure sterility is retort heat treatment—often 120-130° C. for 10 to 20 minutes. Examples of such heat treatments can have $F_0$ values well in excess of the minimum threshold. Other combinations of equivalent heat treatment are known and are applicable to the present invention given appropriate adherence to the requirements of microbial stability and sterility. Other known art non-thermal processes can be used in combination with heat treatment to inhibit microbiological activity in the liquid nutritional composition, for example microfiltration.

In one exemplary embodiment the composition is UHT sterilised at 144° C. for about 6 seconds. In one embodiment the composition is further homogenised after heat treatment at 150/50 bar.

In one exemplary embodiment the composition is subjected to a heat treatment (retort sterilised) at 121° C. for about 10 minutes.

In various embodiments, the heat treatment may comprise a heat treatment with an $F_0$ of 3, such as, 121° C. for 185 s, 130° C. for 23 s, 135° C. for 7.4 s, 140° C. for 2.3 s, 145° C. for 0.73 s, or 150° C. for 0.23 s, a heat treatment with an $F_0$ of 6, such as, 121° C. for 370 s, 130° C. for 46 s, 135° C. for 14.7 s, 140° C. for 4.6 s, 145° C. for 1.46 s, or 150° C. for 0.46 s, or a heat treatment with an $F_0$ of 19.5, such as, 121° C. for 1200 s, 130° C. for 151 s, 135° C. for 47.6 s, 140° C. for 15.1 s, 145° C. for 4.76 s, or 150° C. for 1.51 s.

In one embodiment the heat-treated liquid nutritional composition is filled and packed.

In one embodiment the heat-treated liquid composition is dried. In one embodiment the heat-treated liquid composition is dried to produce a powder. Methods for drying such compositions are known in the art and suitable methods for use herein will be apparent to those skilled in the art. The low viscosity of the heat-treated liquid composition means that the composition may be evaporated to higher solids prior to spray drying without fouling resulting in better energy efficiency and higher throughput.

5. Uses of the Liquid Nutritional Compositions

The liquid nutritional compositions described herein have a high whey protein content. Whey protein has an excellent protein digestibility corrected amino acid score (PDCAAS). It is not only naturally high in essential amino acids and branched chain amino acids but also uniquely high in the amino acid leucine, the amino acid that is thought to be critical to the stimulation of muscle protein synthesis. This high level of leucine, as well as a unique fast digestion profile, enables whey protein to stimulate muscle protein synthesis to a greater extent than casein and/or soy protein in young or older adults.

In various embodiments the liquid nutritional composition is administered to a subject maintain or increase muscle protein synthesis, maintain or increase muscle mass, prevent or increase loss of muscle mass, maintain or increase growth, prevent or decrease muscle catabolism, prevent or treat cachexia, prevent or treat sarcopenia, increase rate of glycogen resynthesis, modulate blood sugar levels, increase insulin response to raised blood glucose concentration, reduce satiety, reduce satiation, increase food intake, increase calorie intake, improve glucose metabolism, increase rate of recovery following surgery, increasing prehabilitation efficacy prior to surgery or chemotherapy, increase rate of recovery following injury, increase rate of recovery following exercise, increase sports performance, and/or provide nutrition.

EXAMPLES

Example 1

This example describes the preparation and properties of liquid nutritional compositions of the invention.

1. Preparation of Liquid Nutritional Compositions

High protein liquid nutritional compositions were prepared as follows. Water was heated to 50° C. and antifoam was added. The protein and carbohydrate ingredients were dry blended, added to the water and allowed to hydrate for at least 60 minutes. A blend of oils and emulsifiers were added. A premix of minerals, trace elements and vitamins were added and dissolved. The pH was adjusted to 6.8 using potassium hydroxide solution and the pre-mix solution was homogenised at 60° C., 150/50 bar. The homogenised mix was UHT sterilised at 140° C. for 6 seconds. The composition of each formulation is provided in Table 1 below. All formulations were nutritionally complete for vitamins and minerals. Milk Protein Concentrate 4882 was a calcium depleted milk protein concentrate manufactured using the method described in PCT/NZ2011/000134, published as WO2012/008858. Whey Protein Concentrate 550 was a heat-denatured whey protein concentrate, manufactured using the method described in PCT/NZ2010/00072, published as WO2010/120199. Whey Protein Concentrate 80 was a native whey protein, obtained by ultrafiltration of cheese whey. The milk protein concentrates and whey protein concentrates are available from Fonterra Co-operative Group Limited.

TABLE 1

Composition of formulations A, B and C

| Ingredients | Amount % wt | | |
|---|---|---|---|
| | A | B | C |
| Water | 59.2 | 54.8 | 53.9 |
| Antifoaming agent Dow Corning 1520 | 0.010 | 0.010 | 0.010 |
| Milk Protein Concentrate 85 (standard MPC) | — | 7.6 | 7.6 |
| Milk Protein Concentrate 4882 | 12.25 | — | — |
| Whey Protein Concentrate 550 | 5.7 | 7.7 | — |
| Whey Protein Concentrate 80 | — | — | 3.4 |
| Maltodextrin (32-36 DE) | 11.9 | 20.3 | 26.1 |
| Sucrose | 1.9 | 1.9 | — |
| Tripotassium citrate monohydrate | 0.075 | 0.167 | 0.268 |
| DiMagnesium phosphate | 0.092 | 0.076 | — |
| Potassium chloride | 0.032 | — | 0.095 |
| Magnesium chloride | — | — | 0.17 |
| Canola oil | 7.5 | 7.2 | 7.7 |
| Lecithin | 0.2 | 0.2 | 0.16 |
| Vitamin premix 11248 Vitablend | 0.14 | — | — |
| Mineral premix 11247 Vitablend | 0.09 | — | — |
| Vanilla 507404T | 0.07 | — | — |
| 5% potassium hydroxide solution | 0.667 | 0.6 | 0.6 |

The nutritional composition of formulations A, B and C and a commercially available formulation of similar protein content, formulation D, is provided in Table 2.

TABLE 2

Nutritional composition of formulations A, B, C and D

| Component | A | B | C | D |
|---|---|---|---|---|
| Energy value (kcal/100 mL) | 200 | 240 | 240 | 240 |
| Protein (g/100 mL) | 16 | 14 | 10 | 14.4 |
| Casein (% wt of total protein) | 55 | 40 | 60 | >90 |
| Whey protein (% wt of total protein) | 45 | 60 | 40 | <10 |
| Lipid (g/100 mL) | 9.0 | 10 | 9.4 | 9.4 |
| Carbohydrates (g/100 mL) | 15.5 | 25.7 | 28.7 | 24.4 |
| Final pH | 6.8 | 6.8 | 6.8 | 6.8 |

2. Analysis of Formulations

No protein aggregation or gelling was observed for Formulations A and B following UHT sterilisation. Both sterilised formulations had a smooth mouth feel.

Formulation C aggregated and gelled extensively during UHT sterilisation. No further analyses on Formulation C were performed.

The viscosity of the formulations at a shear rate of 100 s$^{-1}$ at 20° C. was measured using a rotary viscometer.

Mean particle size (characterised by d[3,2]) was determined for Formulations A and B by static light scattering using a Malvern particle size analyser (Mastersizer 2000, Malvern Instruments Ltd, Malvern, United Kingdom.

To assess the characteristics of the formulations under conditions mimicking those of the upper gastrointestinal tract, an in vitro acidification method was used as described in Schnell (2005). Simulated gastric fluid (SGF) with enzymes was prepared by adding 150 mM NaCl to 1 M Hydrochloric acid, with 3 g of pepsin (porcine gastric mucosa, Sigma P7000) added to this solution before use, with stirring for 30 min. Samples (100 ml) of each liquid nutritional composition were added into a 150 ml beaker and warmed to 37° C. in water bath. SGF was added to the composition, with constant stirring, until the pH dropped to pH 3. The appearance of the mixtures was observed. Results are presented in Table 3.

The above analyses were performed following storage of Formulations A and B and D for at least 4 months at 25° C. Results are shown in Table 4. No creaming, sedimentation or change in taste was observed or detected after storage.

TABLE 3

Analyses of Formulations A, B and C after UHT sterilisation

| | A | B | C |
|---|---|---|---|
| Viscosity (mPa · s) at 100 s$^{-1}$ at 20° C. | 140 | 62 | GEL |
| Mean particle size (d[3, 2]) (μm) | 0.28 | 0.2 | — |
| Coagulation in stomach conditions | Smooth liquid | Smooth Liquid | — |

TABLE 4

Analyses of Formulations A, B and D after at least 4 months storage at 25° C.

| | A | B | D |
|---|---|---|---|
| Viscosity mPa · s at 100 s−1 at 20° C. | 164 | 62 | 113 |
| Mean particle size (d[3, 2]) (μm) | 0.38 | 0.37 | 0.2 |
| Coagulation in stomach conditions | — | — | Coagulated |

Example 2

This example describes the preparation and properties of liquid nutritional compositions. The exemplary nutritional formulations (Table 6) were prepared using denatured WPC powder (WPC550) or native whey powder (WPC 392) detailed in Table 5 and liquid milk protein concentrate at 20% total solids and 18% protein.

High protein liquid nutritional compositions were prepared as follows. Water was heated to 55° C. and antifoam was added. Liquid milk protein concentrate was added to the water. Whey protein concentrate powders were slowly added under agitation and allowed to hydrate for at least 60 minutes. After hydration, solutions were homogenised at 60° C., 150/50 bar. The time of visual aggregation for each formulation at 121° C. was determined. The homogenised mix was then retort sterilised at 121° C. for 3 minutes.

No protein aggregation or gelling was observed for Formulations A1, A2, A3, A4, A5 following retort sterilisation. All sterilised formulations had a smooth mouth feel. The viscosity of the retort formulations at a shear rate of 100 s$^{-1}$ at 20° C. was measured using a rotary viscometer (Table 7). Mean particle size (characterised by d[3,2] and d[4,3]) of formulations before and after retort sterilisation was determined by static light scattering using a Malvern particle size analyser (Mastersizer 2000, Malvern Instruments Ltd, Malvern, United Kingdom (Table 7).

Figure 2:
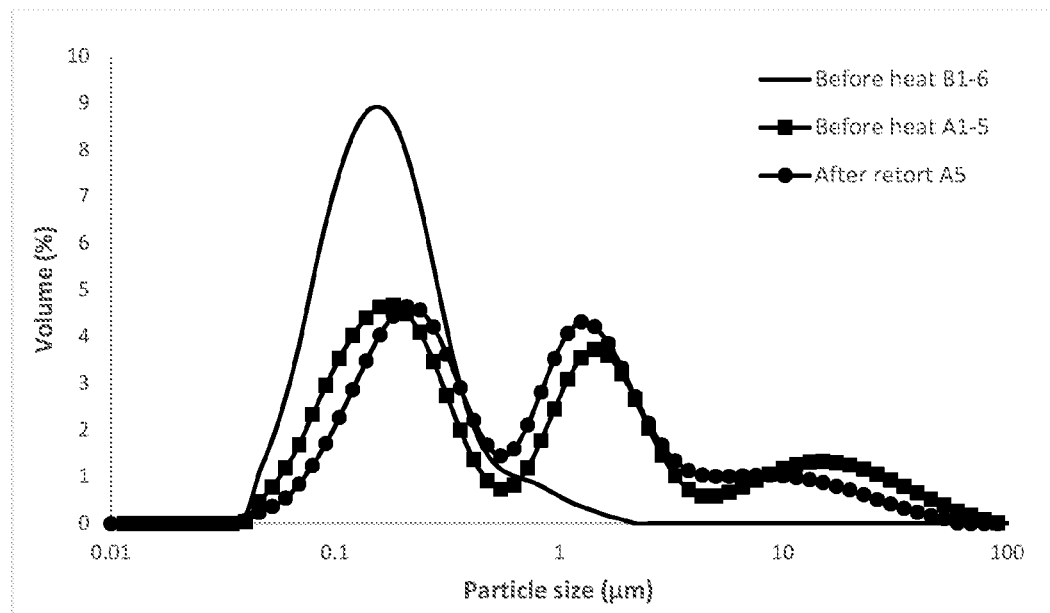
FIG. 2 is a graph showing the particle size of the liquid nutritional compositions prepared using native whey (formulations B1-6), using denatured whey (formulations A1-5) and after retort treatment of A5.

The particle size of the liquid nutritional compositions prepared using native whey (formulations B1-6), using denatured whey (formulations A1-5) and after retort treatment of A5 is shown in FIG. 2.

TABLE 5

Properties of whey protein powders

| Name | Protein Content, % (TN × 6.38) | Residual Denaturable Protein % Total/TN × 6.38 | % Denatured protein | Primary Aggregate Size of 10% TS Protein Solution D[4, 3], μm | Aggregate Growth After Heating 10% TS Protein Solution D[4, 3], μm |
|---|---|---|---|---|---|
| WPC 392[a] | 80.3 | 61 | 0-0.4 | — | Gel |
| WPC 550[b] | 79.1 | 15 | 75 | 1.70 | 1.72 |

[a]Fonterra Co-operative Group Limited, WPC made by ultrafiltration of cheese whey.
[b]Fonterra Co-operative Group Limited, heat denatured WPC made using the method described in PCT/NZ2010/000072; published as W02010/120199

TABLE 6

Composition of formulations A1-5 and B1-6

| | Amount % wt | | | | |
|---|---|---|---|---|---|
| Ingredients | A1 | A2 | A3 | A4 | A5 |
| Water | 59.96 | 53.73 | 47.62 | 41.07 | 34.52 |
| Antifoaming agent Dow Corning 1520 | 0.010 | 0.010 | 0.010 | 0.010 | 0.010 |
| Liquid Milk Protein Concentrate (20% solids, 18% protein) | 32.72 | 37.81 | 42.80 | 48.15 | 53.5 |
| Whey Protein Concentrate 550 | 7.32 | 8.46 | 9.58 | 10.78 | 11.98 |
| Whey Protein Concentrate 392 | — | — | — | — | — |

| | Amount % wt | | | | | |
|---|---|---|---|---|---|---|
| Ingredients | B1 | B2 | B3 | B4 | B5 | B6 |
| Water | 67.09 | 59.96 | 53.73 | 47.62 | 41.07 | 34.52 |
| Antifoaming agent Dow Corning 1520 | 0.010 | 0.010 | 0.010 | 0.010 | 0.010 | 0.010 |
| Liquid Milk Protein Concentrate (20% solids, 18% protein) | 26.8 | 32.72 | 37.81 | 42.80 | 48.15 | 53.5 |
| Whey Protein Concentrate 550 | — | — | — | — | — | — |
| Whey Protein Concentrate 392 | 6.11 | 7.32 | 8.46 | 9.58 | 10.78 | 11.98 |

TABLE 7

Analyses of Formulations A1-5 and B1-6 after retort treatment of 121° C. for 3 mins

| Formulation | Protein content (g/100 ml) | Whey content (g/100 ml) | Casein content (g/100 ml) | pH | Heat coagulation time at 121° C. | Viscosity (cP) at 100 s-1 @ 20 C. after retort at 121° C. for 3 mins | Particle size (μm) [D3, 2] after retort at 121° C. for 3 mins | Particle size (μm) [D4, 3] after retort at 121° C. for 3 mins |
|---|---|---|---|---|---|---|---|---|
| A1 | 12 | 7.2 | 4.8 | 6.7 | >20 min | 6.15 | 0.22 | 1.39 |
| A2 | 14 | 8.4 | 5.6 | 6.65 | >20 min | 10 | 0.25 | 1.97 |
| A3 | 16 | 9.6 | 6.4 | 6.65 | >20 min | 16.1 | 0.27 | 2.27 |
| A4 | 18 | 10.8 | 7.2 | 6.6 | 10.5 min | 36.3 | 0.35 | 2.80 |
| A5 | 20 | 12 | 8 | 6.6 | 4.5 min | 154 | 0.44 | 3.62 |
| B1 | 10 | 6.0 | 4.0 | 6.7 | 2.1 min | GEL | GEL | GEL |
| B2 | 12 | 7.2 | 4.8 | 6.7 | 56 s | GEL | GEL | GEL |
| B3 | 14 | 8.4 | 5.6 | 6.65 | 45 s | GEL | GEL | GEL |

Results

The formulations comprising denatured WPC (WPC550), showed superior heat stability compared with a native WPC (392) as shown in Table 7. These results show that the liquid nutritional formulations comprising very high protein (A1-5, even at 20% protein) are heat stable following the heat treatment having an F0 value of 3 (121° C. for 3 mins), while all the formulations containing same amount of undenatured, native whey (WPC392) formed gel after the same heat treatment of retort processing having an F0 value of 3 (121° C. for 3 mins). FIG. 2 shows that liquid nutritional compositions comprising denatured whey protein (A1-5) have a mean particle size of ~3 μm as characterised by d[4,3] before heat treatment and the mean particle size does not change after the retort treatment even at the total protein content of 20%. On the contrary, liquid nutritional compositions comprising native whey protein (B1-6) have a mean particle size of ~0.2 μm as characterised by d[4,3] before heat treatment and they formed a gel even at the total protein content of 10% after retort treatment.

Example 3

Liquid nutritional formulations of 1.5 kcal/mL, comprising 6% total protein was prepared as shown in Table 8, following the method of FIG. 1. The whey protein and non-whey protein (casein) were present in all the liquid nutritional compositions in a weight ratio of 60:40. The whey protein is provided by an ingredient either by denatured WPC (WPC 550) or native WPC (WPC392). The pH of all the formulations were adjusted to pH 6.8.

The level of minerals (sodium, potassium, calcium, magnesium) in the final composition were matched at the same concentration for formulation A and B, and higher magnesium levels were applied for formulation C (Table 9). Those levels were selected according to the European Commission guideline on Food for Special Medical Purposes (FSMP) directive.

High protein liquid nutritional compositions were prepared as follows. Water was heated to 50° C. and antifoam was added. The protein and carbohydrate ingredients were dry blended, added to the water and allowed to hydrate for at least 60 minutes. A blend of oils and emulsifiers were added. A premix of minerals, trace elements and vitamins were added and dissolved. The pH was adjusted to 6.8 using potassium hydroxide solution and the pre-mix solution was homogenised at 60° C., 150/50 bar. Each homogenised mix was then heat sterilised using retort process as provided in Table 8 below. Milk Protein Concentrate 4882 was a calcium depleted milk protein concentrate manufactured using the method described in PCT/NZ2011/000134, published as WO2012/008858. Whey Protein Concentrate 550 was a heat-denatured whey protein concentrate, manufactured using the method described in PCT/NZ2010/00072, published as WO2010/120199. The milk protein concentrates and whey protein concentrates are available from Fonterra Co-operative Group Limited.

TABLE 8

Composition of formulations A, B, C,

| Ingredients | Amount % wt | | |
|---|---|---|---|
| | A | B | C |
| Water | 68.86 | 68.93 | 68.93 |
| Antifoaming agent | 0.010 | 0.010 | 0.010 |
| Milk Protein Concentrate 4882 | 3.406 | 3.406 | 3.406 |
| Whey Protein Concentrate 550 | — | 3.494 | 3.494 |
| Whey Protein Concentrate 392 | 3.495 | — | — |
| Maltodextrin (40 DE) | 15.98 | 15.98 | 15.98 |
| Sucrose | 1.9 | 1.9 | 1.9 |
| Tricalcium phosphate | 0.165 | 0.141 | 0.141 |
| Tripotassium citrate monohydrate | 0.1 | 0.1 | 0.1 |
| DiMagnesium phosphate | 0.181 | 0.171 | 0.171 |
| Potassium chloride | 0.173 | 0.148 | 0.148 |
| Sodium chloride | 0.051 | — | — |
| Magnesium chloride | — | — | 0.285 |
| Canola oil | 4.7 | 4.739 | 4.739 |
| Lecithin | 0.079 | 0.079 | 0.079 |
| Carrageenan | 0.03 | 0.03 | 0.03 |
| Vitamin & mineral premix | 0.401 | 0.401 | 0.401 |
| Vanilla flavour | 0.068 | 0.068 | 0.068 |
| 5% potassium hydroxide solution | 0.4 | 0.4 | 0.4 |
| Heat treatment | Retort 121° C. for 3 mins | Retort 121° C. for 10 mins | Retort 121° C. for 10 mins |
| $F_0$ | 3 | 6 | 6 |

TABLE 9

Mineral composition of the liquid nutritional compositions

| Component | A | B | C |
|---|---|---|---|
| Sodium (mg/100 mL) | 75 | 75 | 75 |
| Potassium (mg/100 mL) | 180 | 180 | 180 |
| Calcium (mg/100 mL) | 137 | 137 | 137 |
| Magnesium (mg/100 mL) | 32 | 32 | 67 |

Results

The results show that the liquid nutritional formulations comprising a native WPC (Formulation A) is not heat stable at 6% total protein (60:40 whey to casein ratio) following the heat treatment having an $F_0$ value of 3 (Table 10). The formulations comprising denatured WPC (Formulations B and C), showed superior heat stability even after a heat treatment having an $F_0$ value of 6.

It is well known in the art that soluble divalent ions promote whey protein aggregation and cause gelation by forming bridging reaction between whey protein molecules. The formulation comprising twice as much soluble magnesium (provided by Magnesium chloride) in the final formulation (Formulation C) was still stable after heat treatment having an $F_0$ value of 6.

TABLE 10

Analyses of formulations after heat treatment

| | | A | B | C |
|---|---|---|---|---|
| After heat treatment | Viscosity (mPa · s) at 100 s$^{-1}$ at 20° C. | GEL | 24 | 34 |
| | Mean particle size (d [3, 2]) (µm) | GEL | 0.38 | 0.38 |
| | Mean particle size (d[4, 3]) (µm) | GEL | 1.76 | 3.6 |

Example 4

High protein liquid nutritional compositions were prepared as follows. Water was heated to 50° C. and antifoam was added. The protein and carbohydrate ingredients were dry blended, added to the water and allowed to hydrate for at least 60 minutes. A blend of oils and emulsifiers were added. A premix of minerals, trace elements and vitamins were added and dissolved. The pH was adjusted to 6.8 using potassium hydroxide solution and the pre-mix solution was homogenised at 60° C., 150/50 bar.

The composition of each formulation is provided in Table 11 below. Milk Protein Concentrate 4882 was a calcium depleted milk protein concentrate manufactured using the method described in PCT/NZ2011/000134, published as WO2012/008858. Milk Protein Concentrate 4861 was a calcium depleted milk protein concentrate manufactured using the method described in PCT/NZ2011/000134, published as WO2012/008858. Whey Protein Concentrate 550 was a heat-denatured whey protein concentrate, manufactured using the method described in PCT/NZ2010/00072, published as WO2010/120199. The milk protein concentrates and whey protein concentrate are available from Fonterra Co-operative Group Limited.

Each homogenised mix was heat sterilised as described in Table 8.

TABLE 11

Composition of formulations A, B, C, D, E, F, G, H

| Ingredients | A | B | C | D | E | F | G | H |
|---|---|---|---|---|---|---|---|---|
| Water | 68.28 | 53.6 | 53.7 | 53.8 | 53.3 | 51.55 | 76.09 | 74.17 |
| Antifoaming agent | 0.010 | 0.010 | 0.010 | 0.010 | 0.010 | 0.010 | 0.010 | 0.010 |
| Milk Protein Concentrate 85 (standard MPC) | — | — | — | — | — | — | 14.69 | 16.17 |
| Milk Protein Concentrate 4882 | — | 5.21 | 3.26 | 5.43 | 7.95 | — | — | — |
| Milk Protein Concentrate 4861 | 3.52 | — | — | — | — | 8.71 | — | — |
| Whey Protein Concentrate 550 | 3.65 | 5.427 | 7.35 | 5.57 | 8.16 | 9.02 | 6.74 | 7.42 |
| Soy protein isolate | — | — | — | 1.95 | — | — | — | — |
| Maltodextrin (36-40 DE) | 16.07 | 23.84 | 23.86 | 20.99 | 18.19 | 18.65 | — | — |
| Sucrose | 1.9 | 1.6 | 1.6 | 1.6 | 1.9 | 1.9 | — | — |
| Trehalose | — | — | — | — | — | — | 1.24 | 1.05 |
| Tricalcium phosphate | 0.125 | 0.137 | 0.137 | 0.137 | 0.052 | 0.158 | — | — |
| Tripotassium citrate monohydrate | 0.205 | 0.27 | 0.27 | 0.27 | 0.059 | 0.06 | — | — |
| DiMagnesium phosphate | 0.171 | — | — | — | 0.088 | 0.09 | 0.087 | 0.087 |
| Potassium chloride | 0.076 | 0.07 | — | 0.072 | 0.03 | 0.05 | — | — |
| Magnesium chloride | — | 0.17 | — | 0.166 | 0.053 | 0.03 | — | — |
| Canola oil | 4.8 | 8.0 | 7.9 | 8.3 | 8.27 | 7.52 | 0.83 | 0.76 |
| Lecithin | 0.13 | 0.13 | 0.13 | 0.13 | 0.13 | 0.13 | 0.02 | 0.02 |
| Novagel 1518 | — | 0.20 | 0.2 | — | — | — | — | — |
| Carageenan | 0.03 | — | — | — | — | — | — | — |
| Gellan gum | — | 0.015 | 0.015 | — | — | — | — | — |
| Vitamin premix | 0.022 | 0.132 | — | — | 0.130 | 0.134 | — | — |
| Mineral premix | 0.055 | 0.089 | — | — | 0.089 | 0.09 | — | — |
| Vitamin & mineral premix | — | — | 0.614 | 0.614 | — | — | 0.25 | — |
| Choline chloride | 0.074 | 0.074 | 0.074 | 0.075 | 0.075 | 0.075 | — | — |
| Vanilla flavour | 0.068 | 0.158 | — | — | 0.158 | 0.158 | — | — |
| 5% potassium hydroxide solution | 0.40 | 0.92 | 0.92 | 0.92 | 1.336 | 1.667 | 0.22 | 0.31 |

The nutritional composition and type of heat treatment of formulations A, B, C, D, E, F, G, H is provided in Table 12.

TABLE 12

Nutritional composition of formulations (A, B, C, D, E, F, G, H)

| Component | A | B | C | D |
|---|---|---|---|---|
| Energy value (kcal/100 mL) | 150 | 240 | 240 | 240 |
| Protein (g/100 mL) | 6 | 9.6 | 9.6 | 12 |
| Casein (% wt of total protein) | 40 | 40 | 25 | 34 |
| Whey protein (% wt of total protein) | 60 | 60 | 75 | 50 |
| Non-dairy protein (% wt of total protein) | — | — | — | 16 |
| Fat (g/100 mL) | 5.5 | 9.6 | 9.6 | 10 |
| Carbohydrates (g/100 mL) | 19 | 28.7 | 28.7 | 25.4 |
| Sodium (mg/100 mL) | 60 | 78 | 92 | 104 |
| Potassium (mg/100 mL) | 160 | 234 | 185 | 225 |
| Calcium (mg/100 mL) | 120 | 168 | 132 | 160 |
| Magnesium (mg/100 mL) | 30 | 30 | 6 | 30 |
| Final pH | 6.8 | 6.8 | 6.8 | 6.8 |
| Heat treatment | UHT 144° C. for 6 sec $F_0 = 19.5$ | UHT 144° C. for 6 sec $F_0 = 19.5$ | Retort 121° C. for 10 mins $F_0 = 6$ | Retort 121° C. for 3 mins $F_0 = 3$ |
| Minor components | All the compositions are nutritionally complete in vitamins and trace elements | | | |

| Component | E | F | G | H |
|---|---|---|---|---|
| Energy value (kcal/100 mL) | 240 | 240 | 100 | 110 |
| Protein (g/100 mL) | 14.4 | 16 | 18 | 20 |
| Casein (% wt of total protein) | 40 | 40 | 55 | 55 |
| Whey protein (% wt of total protein) | 60 | 60 | 45 | 45 |

TABLE 12-continued

Nutritional composition of formulations (A, B, C, D, E, F, G, H)

| | | | | |
|---|---|---|---|---|
| Non-dairy protein (% wt of total protein) | — | — | — | — |
| Fat (g/100 mL) | 10 | 10 | 1.5 | 1.5 |
| Carbohydrates (g/100 mL) | 25.7 | 15.5 | 3.3 | 3.3 |
| Sodium (mg/100 mL) | 145 | 149 | 53 | 58 |
| Potassium (mg/100 mL) | 145 | 184 | 111 | 120 |
| Calcium (mg/100 mL) | 168 | 240 | 355 | 395 |
| Magnesium (mg/100 mL) | 30 | 31 | 20 | 22 |
| Final pH | 6.8 | 6.8 | 6.7 | 6.66 |
| Heat treatment | UHT 144° C. for 6 sec F0 = 19.5 | UHT 144° C. for 6 sec F0 = 19.5 | UHT 140 C. for 3 sec F0 = 3 | UHT 140 C. for 3 sec F0 = 3 |
| Minor components | All the compositions are nutritionally complete in vitamins and trace elements | | | |

No protein aggregation or gelling was observed for Formulations A, B, C, D, E, F, G, H following heat sterilisation. All sterilised formulations had a smooth mouth feel.

The viscosity of the formulations at a shear rate of $100\ s^{-1}$ at 20° C. was measured using a rotary viscometer (Table 13). Mean particle size (characterised by d[3,2] and d[4,3]) was determined for Formulations A and B by static light scattering using a Malvern particle size analyser (Mastersizer 2000, Malvern Instruments Ltd, Malvern, United Kingdom (Table 13).

The above analyses were performed following storage for at least six months at 25° C. No creaming, sedimentation or change in taste—was observed after storage.

TABLE 13

Analyses of formulations after heat treatment

| | A | B | C | D | E | F | G | H |
|---|---|---|---|---|---|---|---|---|
| Viscosity (mPa · s) at 100 s$^{-1}$ at 20° C. | 23.3 | 68 | 57.4 | 159 | 73.4 | 147 | 54 | 96.3 |
| Mean particle size (d[3, 2]) (μm) | 0.58 | 0.4 | 0.30 | 0.8 | 0.49 | 0.33 | 0.17 | 0.18 |
| Mean particle size (d[4, 3]) (μm) | 6.8 | 1.08 | 1.83 | 6.4 | 1.31 | 1.74 | 0.50 | 0.52 |

Example 5

To assess the characteristics of the formulations under conditions mimicking those of the upper gastrointestinal tract, an in vitro acidification method was used as described in Schnell (2005).

Three liquid nutritional composition described in Example 3 (A, B, E) and 3 commercial liquid nutritional composition (Com1, Com2, Com3) described in Table 14 were selected for comparison.

Simulated gastric fluid (SGF) containing enzymes was prepared by adding 150 mM NaCl to 1 M Hydrochloric acid, with 3 g of pepsin (porcine gastric mucosa, Sigma P7000) added to this solution before use, with stirring for 30 min. Samples (100 ml) of each liquid nutritional composition were added into a 150 ml beaker and warmed to 37° C. in water bath. SGF was added to the composition, with constant stirring, until the pH dropped to pH<3. The appearance of the mixtures was observed. Results are presented in Table 14.

TABLE 14

Nutritional composition, shelf life stability and gastrointestinal stability of liquid nutritional compositions compared to commercial formulations

| Component | A | B | E |
|---|---|---|---|
| Energy value (kcal/100 mL) | 150 | 240 | 240 |
| Protein (g/100 mL) | 6 | 9.6 | 14.4 |
| Casein (% wt of total protein) | 40 | 40 | 40 |
| Whey protein (% wt of total protein) | 60 | 60 | 60 |
| Fat (g/100 mL) | 5.5 | 9.6 | 10 |
| Carbohydrates (g/100 mL) | 19 | 28.7 | 25.7 |
| Viscosity (mPa · s) at 100 s−1 at 20° C. at 6 months shelf life | 23.2 | 71.3 | 65.8 |
| Mean particle size (d[3, 2]) (μm) at 6 months shelf life | 0.45 | 0.40 | 0.44 |
| Coagulation in stomach conditions | Smooth liquid | Smooth liquid | Smooth liquid |

| Component | Com1 | Com2 | Com3 |
|---|---|---|---|
| Energy value (kcal/100 mL) | 150 | 240 | 240 |
| Protein (g/100 mL) | 6 | 9.6 | 14.4 |
| Casein (% wt of total protein) | >95 | >80 | >80 |
| Whey protein (% wt of total protein) | <5 | <20 | <20 |
| Fat (g/100 mL) | 5.5 | 9.6 | 10 |
| Carbohydrates (g/100 mL) | 19 | 28.7 | 25.7 |
| Viscosity (mPa · s) at 100 s−1 at 20° C. at 6 months shelf life | 17.7 | 53.4 | 104 |
| Mean particle size (d[3, 2]) (μm) at 6 months shelf life | 0.13 | 0.25 | 0.2 |
| Coagulation in stomach conditions | Coagulated gel | Coagulated gel | Coagulated gel |

Method for In-Vitro Digestion Examination:

A Human Gastric Simulator (HGS) developed by Kong and Singh (2010) was used for in-vitro digestion model. 150 ml of liquid nutritional compositions (A, B, E, Com1, Com2, Com3) was mixed with 19.2 mL Simulated Gastric Fluid (SGF) and 4.8 mL enzyme solution (pepsin 16 mg/mL and amamo lipase A 2 mg/mL) prior to fed into the HGS. After warmed up to 37° C., the nutritional compositions started being digested by the enzymes and SGF pumped in at flow rate of 0.6 and 2.4 mL per min, respectively. For accurate control of the gastric emptying, digesta samples (60 mL) was removed from the HGS at every 20 min, equaling the gastric emptying rate of 3.0 ml/min. The contraction frequency was 3 times/min, simulating the actual contraction of the stomach. The temperature of the HGS was maintained at 37° C. by a heater and thermostat. The maximum digestion time was 220 min.

At each time interval, the sample was removed from the HGS and then filtered through a mesh with a pore size of 1 mm in diameter for further analysis, so that only the solid mass of size <1 mm was emptied. In addition, to observe the effect of mechanical processing alone on the digestion, experiments were carried out without the addition of pepsin (only SGF) as controls. Measurement of the pH and weight of the curd observations were carried out immediately before the pepsin inactivation.

pH Measurement

The initial pH in the HGS was defined as the pH of the nutritional compositions. With the ingestion of SGF (2.4 mL/min) and gastric emptying (3 mL/min), the pH in the HGS at different times was assumed to be that of the emptied digesta collected at every 20 min.

Weight of Clot

After 20, 60, 120 and 220 mins digestion time, the curd (if any) was collected and passed through a filter with a 1 mm pore size to separate the clot and the aqueous phase. The clots were then rinsed with SGF to remove pepsin from the surface and weighed immediately (Table 15). It was then heated to 90° C. for 3 min to inactivate the pepsin. Images of curds were obtained (not shown) from 150 ml of commercial liquid nutritional compositions after 20, 60, 120 and 220 min of digestion in the human gastric simulator. No curd was formed for any of the liquid nutritional composition of this invention at any time point of the digestion.

Determination of Average Droplet Size

The mean particle size and the particle size distribution of the samples obtained from the HGS were measured during digestion, using Malvern MasterSizer 2000 (Malvern Instruments Ltd., Malvern, Worcestershire, UK). The particle size of the digested samples was characterised using surface average diameter [$d_{3,2}$ (μm)] or the volume-surface average diameter [$d_{4,3}$ (μm)].

Results for In-Vitro Digestion:

The emptied digesta from all the liquid nutritional compositions with varying protein content (6, 9.6 and 14.4%) and composition showed a similar decrease rate in pH from around 6.8 to <pH 3 over the digestion period of 220 mins. Therefore, the differences observed in the digestion behaviour of liquid nutritional compositions are not due to pH decrease rate but rather related to the protein composition.

TABLE 15

Weight of the coagulants obtained from 150 ml of liquid nutritional compositions during different time points of digestion in the human gastric simulator.

| Liquid nutritional compositions | Digestion time (mins) | | | |
|---|---|---|---|---|
| | 20 | 60 | 120 | 220 |
| A | None | None | None | None |
| B | None | None | None | None |
| E | None | None | None | None |
| Com1 | 5.1 g | 17.6 g | 13.7 g | 4.9 g |
| Com2 | 2 g | 8.4 g | 4.4 g | 0.5 g |
| Com3 | 133.5 g | 80 g | 39.4 g | 5.8 g |

For all the commercial liquid nutritional compositions containing casein as the main source of protein (at least 80% w/w of the protein coming from caseins), protein coagulation was evident in the first 20 min of digestion and remained to be apparent until the end of digestion time. No curd formation was observed for any of the liquid nutritional compositions developed using this invention. Compositions A, B, and E stays in a liquid phase under stomach conditions of adults. Coagulated proteins can delay gastric emptying since the curd behaves like a solid in the stomach. This example shows that the liquid nutritional compositions of this invention likely to leave the stomach faster.

Figure 3:
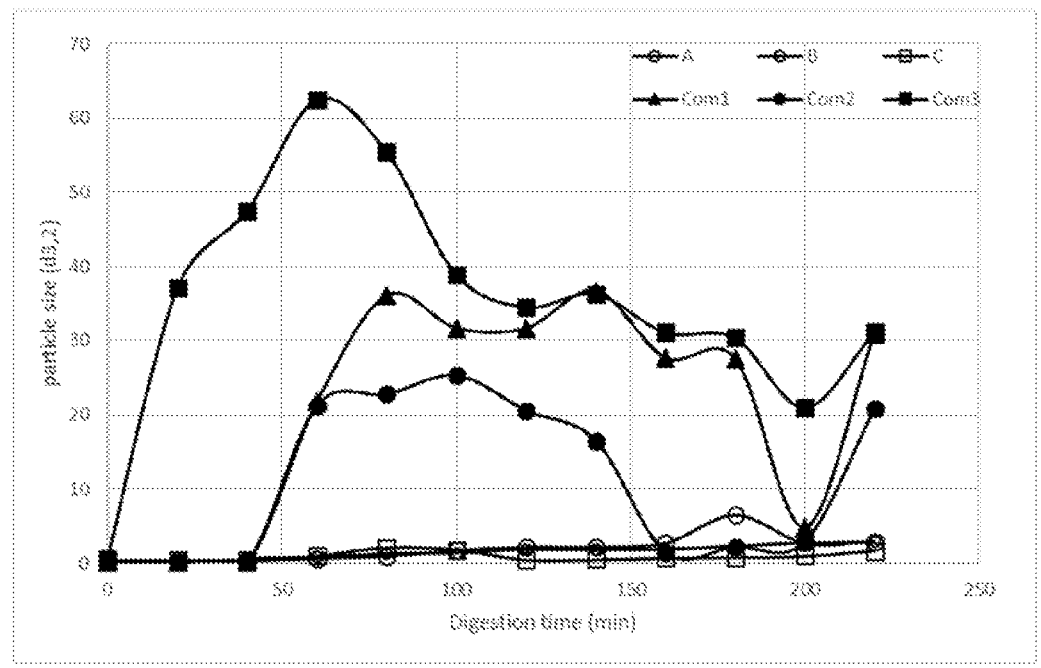
FIG. 3 is a graph showing changes in particle size ($d_{3,2}$) during gastric digestion of different liquid nutritional compositions containing 6%, 9.6% and 14.4% protein in a human gastric simulator.

The changes in the average particle size ($d_{3,2}$) of the liquid nutritional composition samples under dynamic digestion in the HGS are shown in FIG. 3. The particle size of the three commercial liquid nutritional compositions containing casein as the main source of protein (at least 80% w/w of the protein coming from caseins) showed drastic increase in the particle size during digestion. This increase in particle size indicates the aggregation of proteins and the flocculation of oil droplets due to low pH and/or the action of enzymes. In contrast, composition A, B and E showed almost no change in particle size throughout the whole digestion time.

Any documents referred to herein including, but not limited to, patents, patent applications, journal articles, books, and the like, are incorporated herein by reference in their entirety. Any section headings used herein are for organizational purposes only and are not to be construed as limiting the subject matter described.

Although the invention has been described by way of example and with reference to particular embodiments, it is to be understood that modifications and/or improvements may be made without departing from the scope or spirit of the invention.

INDUSTRIAL APPLICATION

The liquid nutritional compositions described herein are useful for providing nutrition to a subject in need thereof. Applications of the liquid nutritional compositions include medical foods, enteral nutrition, food for special medical purposes, liquid meal replacers and supplements.

The invention claimed is:

1. A heat-treated, shelf-stable liquid nutritional composition having a pH of from 6.6 to about 8.0, the composition comprising
   a total protein content of at least about 9 g per 100 mL of the composition, the total protein content comprising
   a) whey protein comprising or provided by an ingredient that comprises heat-denaturable protein of which at least about 55% is present in a denatured state, wherein the whey protein in a denatured state comprises microparticles having a volume weighted mean diameter D [4,3] of less than about 7 μm, and
   b) non-whey protein comprising or consisting of casein, or one or more non-dairy proteins, or casein and one or more non-dairy proteins,
   wherein the whey protein has a degree of hydrolysis of less than about 4%, and the whey protein and the non-whey protein are present in a weight ratio of from about 45:55 to about 80:20; and
   wherein the liquid nutritional composition exhibits substantially no gelation or aggregation when subjected to a heat treatment having an $F_0$-value of at least 3.

2. A liquid nutritional composition of claim 1, wherein the total protein content of the composition comprises at least about 10 g, or 12 g protein per 100 mL of the composition.

3. A liquid nutritional composition of claim 1, wherein the whey protein is non-hydrolysed.

4. A liquid nutritional composition of claim 1, wherein the whey protein comprises or is provided by an ingredient that comprises heat-denaturable protein of which at least about 65% is present in a denatured state.

5. A liquid nutritional composition of claim 1, wherein the non-whey protein comprises or consists of casein.

6. A liquid nutritional composition of claim 1, wherein the casein comprises or is provided by an ingredient comprising non-micellar casein, micellar casein or non-micellar and micellar casein.

7. A liquid nutritional composition of claim 1, wherein the casein comprises or is provided by an ingredient comprising milk protein isolate (MPI), milk protein concentrate (MPC), micellar casein isolate (MCI), micellar casein concentrate (MCC), proteins of liquid condensed milk, skim milk, skim milk powder, condensed skim milk, whole milk, whole milk powder, a caseinate, total milk protein (TMP), milk co-precipitates, an MPC or MPI that has been modified to dissociate casein micelles, calcium-chelated casein micelles, a charge-modified casein, a casein ingredient comprising: MPC or MPI, where at least a portion of the calcium or phosphate or both the calcium and phosphate has been replaced with sodium, potassium, zinc, magnesium and like, or a combination of any two or more thereof; a glycosylated casein or a combination of any two or more thereof.

8. A liquid nutritional composition of claim 7, wherein the caseinate comprises sodium caseinate, calcium caseinate, magnesium caseinate, potassium caseinate or a combination of any two or more thereof.

9. A liquid nutritional composition of claim 1, wherein the non-dairy protein comprises plant protein or hydrolysed plant protein.

10. A liquid nutritional composition of claim 9, wherein the plant protein or hydrolysed plant protein comprises canola, rapeseed, pea, chickpea, bean, lupin, lentil, soy, rice, wheat, sorghum, maize, corn, barley, almond, cashew, chia, hemp, linseed protein or flax protein, a hydrolysed form thereof, or a combination of any two or more thereof.

11. A liquid nutritional composition of claim 1, wherein the composition
    a) comprises from about 0.01 to about 10 g non-dairy protein per 100 mL of the composition, or
    b) comprises from about 0.01 to about 25 g lipid per 100 mL of the composition, or
    c) comprises from about 0.01 to about 45 g carbohydrate per 100 mL of the composition, or
    d) has an energy density of from about 50 to about 400 kcal per 100 mL of the composition, or
    e) comprises less than about 4 g per 100 mL of the composition of di-, oligo-, and/or poly-saccharides that comprise one glucose unit or no glucose units, or any combination of any two or more of a) to e).

12. A liquid nutritional composition of claim 1, wherein casein comprises from about 5% to about 65% by weight of the total protein.

13. A liquid nutritional composition of claim 1, wherein the composition
    a) has a viscosity of less than about 500 mPa.s when measured at a temperature of 20° C. and a shear rate of 100 s$^{-1}$, or
    b) has an average particle size of less than about 7 µm as categorised by the surface weighted average particle size parameter d[3,2] and/or the volume weighted mean diameter D[4,3], or
    a combination of a) and b).

14. A method of preparing a heat-treated, shelf-stable liquid nutritional composition, the method comprising
    a) providing a liquid composition having a pH of between 6.6 and 8.0, the composition comprising a total protein content of at least about 9 g per 100 ml of the composition,
    the total protein content comprising
        i) whey protein comprising or provided by an ingredient that comprises heat-denaturable protein of which at least about 55% is present in a denatured state, wherein the whey protein in a denatured state comprises microparticles having a volume weighted mean diameter D[4,3] of less than about 7 pm, and
        ii) non-whey protein comprising or consisting of casein, or one or more non-dairy proteins, or casein and one or more non-dairy proteins,
    wherein the whey protein has a degree of hydrolysis of less than about 4%, and the whey protein and the non-whey protein are present in a weight ratio of from about 45:55 to about 80:20; and
    b) subjecting the liquid composition to a heat treatment having an Fo-value of at least 3 to prepare the heat-treated liquid nutritional composition, wherein the heat-treated liquid nutritional composition exhibits substantially no gelation or aggregation, and
    c) optionally drying the heat-treated liquid nutritional composition.

15. A method of claim 14, wherein the heat-treated liquid nutritional composition
    a) has a viscosity of less than about 500 mPa.s when measured at 20° C. and shear rate of 100 s$^{-1}$, or
    b) has an average particle size of less than about 7 µm as categorised by the surface weighted average particle size parameter d[3,2] and/or the volume weighted mean diameter D[4,3], or
    c) exhibits essentially no observable gelation or aggregation, or
    d) any combination of any two or more of (a) to (c) above.

16. A method of maintaining or increasing muscle protein synthesis, maintaining or increasing muscle mass, preventing or reducing loss of muscle mass, maintaining or increasing growth, preventing or decreasing muscle catabolismpreventing or treating cachexia, preventing or treating sarcopenia, increasing rate of glycogen resynthesis, modulating blood sugar levels, increasing insulin response to raised blood glucose concentration, reducing satiety, reducing satiation, reducing food intake, reducing calorie intake, improving glucose metabolism, increasing rate of recovery following surgery, increasing prehabilitation efficacy prior to surgery or chemotherapy, increasing rate of recovery following injury, increasing rate of recovery following exercise, increasing sports performance, and/or providing nutrition to a subject in need thereof, the method comprising administering to the subject a liquid nutritional composition of claim 1.

17. A liquid nutritional composition of claim 1, wherein
    a) the total protein content of the composition comprises at least about 12 g protein per 100 mL of the composition, and
    b) the composition has an energy density of at least about 200 kcal per 100 mL of the composition.

18. A liquid nutritional composition of claim 17, wherein the liquid nutritional composition has a pH of 6.6 to 7.5.

19. A liquid nutritional composition of claim 1, wherein the liquid nutritional composition has a pH of 6.6 to 7.5.

20. A liquid nutritional composition of claim 1, wherein the composition comprises a total amount of monovalent metal ions of at least about 12 mg/g protein, at least about 25 mg/g protein; or at least about 40 mg/g protein.

21. The liquid nutritional composition of claim 1, wherein the non-whey protein is an animal protein.

22. The liquid nutritional composition of claim 21, wherein the animal protein is collagen.

23. The method of claim 14, wherein the non-whey protein is an animal protein.

24. The method of claim 23, wherein the animal protein is collagen.

* * * * *

UNITED STATES PATENT AND TRADEMARK OFFICE
CERTIFICATE OF CORRECTION

PATENT NO. : 12,274,285 B2
APPLICATION NO. : 17/309310
DATED : April 15, 2025
INVENTOR(S) : Esra Cakir-Fuller et al.

Page 1 of 2

It is certified that error appears in the above-identified patent and that said Letters Patent is hereby corrected as shown below:

In the Specification

Column 2, Line 10, delete "food intake" and insert -- food intake. --

Column 25, Line 1, delete "to 140°° C. for" and insert -- to 140° C. for --.

Column 29-30, Line 13 (approx.) (TABLE 7), delete

" B3    14    8.4    5.6    6.65    45 s    GEL    GEL    GEL " and insert

| B3 | 14 | 8.4 | 5.6 | 6.65 | 45 s | GEL | GEL | GEL |
| B4 | 16 | 9.6 | 6.4 | 6.65 | 40 s | GEL | GEL | GEL |
| B5 | 18 | 10.8 | 7.2 | 6.6 | 38 s | GEL | GEL | GEL |
| B6 | 20 | 12 | 8 | 6.6 | 38 s | GEL | GEL | GEL |

--.

Column 33, Line 24 (approx.) (TABLE 11), delete "Carageenan" and insert -- Carrageenan --.

Column 34, Line 23 (approx.) (TABLE 11-continued), delete "Carageenan" and insert
-- Carrageenan --.

Column 36, Line 64, delete "and amamo lipase" and insert -- and amano lipase --.

In the Claims

Column 38, Claim 1, Line 50, delete "comprises heat -denaturable protein" and insert -- comprises heat-denaturable protein --.

Column 38, Claim 1, Line 54, delete "diameter D [4,3] of" and insert -- diameter D[4,3] of --.

Column 40, Claim 14, Line 5, delete "100 ml of" and insert -- 100 mL of --.

Signed and Sealed this
Twenty-ninth Day of July, 2025

Coke Morgan Stewart
*Acting Director of the United States Patent and Trademark Office*

Column 40, Claim 14, Line 9, delete "comprises heat -denaturable protein" and insert -- comprises heat-denaturable protein --.

Column 40, Claim 14, Line 22, delete "an Fo-value of" and insert -- an $F_0$-value of --.

Column 40, Claim 14, Line 24, delete "the heat -treated liquid" and insert -- the heat-treated liquid --.

Column 40, Claim 16, Lines 42-43, delete "muscle catabolismpreventing or" and insert -- muscle catabolism, preventing or --.